(12) United States Patent
Zoller et al.

(10) Patent No.: US 7,897,616 B2
(45) Date of Patent: Mar. 1, 2011

(54) IMIDAZOPYRIDIN-2-ONE DERIVATIVES AS INHIBITORS OF LIPASES AND PHOSPHOLIPASES

(75) Inventors: Gerhard Zoller, Frankfurt am Main (DE); Stefan Petry, Frankfurt am Main (DE); Markus Follmann, Wülfrath (DE); Gunter Muller, Frankfurt am Main (DE); Norbert Tennagels, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 234 days.

(21) Appl. No.: 12/235,053

(22) Filed: Sep. 22, 2008

(65) Prior Publication Data

US 2009/0076068 A1    Mar. 19, 2009

Related U.S. Application Data

(63) Continuation of application No. PCT/EP2007/002637, filed on Mar. 26, 2007.

(30) Foreign Application Priority Data

Mar. 28, 2006 (DE) .................. 10 2006 014 685

(51) Int. Cl.
*C07D 471/04* (2006.01)
*A61K 31/437* (2006.01)
(52) U.S. Cl. ..................... 514/303; 546/118
(58) Field of Classification Search ............... 546/118; 514/303
See application file for complete search history.

(56) References Cited

U.S. PATENT DOCUMENTS 4,144,341 A    3/1979    Clark et al.

FOREIGN PATENT DOCUMENTS

| WO | WO 02/30886 | 4/2002 |
| WO | WO 2005/073199 | 8/2005 |
| WO | WO 2006/022954 | 3/2006 |
| WO | WO 2006/097808 | 9/2006 |
| WO | WO 2006/131231 | 12/2006 |

OTHER PUBLICATIONS

Hcaplus 1979:145541 abstract, "Synthesis and analgesic activity of 1,3-dihydro-3-(substituted phenyl) imidazo [4,5-b]pyridines", Clark et. al., 1978.*

* cited by examiner

*Primary Examiner*—Zinna N Davis
(74) *Attorney, Agent, or Firm*—Scully, Scott, Murphy & Presser, P.C.

(57) ABSTRACT

The present invention relates to imidazopyridin-2-one derivatives of the formula I with the definitions specified in the description, to their pharmaceutically usable salts and to their use as medicaments.

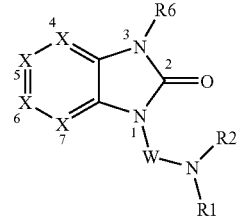

9 Claims, No Drawings

IMIDAZOPYRIDIN-2-ONE DERIVATIVES AS INHIBITORS OF LIPASES AND PHOSPHOLIPASES

This application is a Continuation of International Application No. PCT/EP2007/002637, filed Mar. 26, 2007, which is incorporated herein by reference in its entirety.

FIELD OF THE INVENTION

The present invention relates to imidazopyridin-2-one derivatives of the formula I, to their pharmaceutically usable salts and to their use as medicaments.

BACKGROUND OF THE INVENTION

In addition to the imidazopyridin-2-one derivatives described in the present application, structurally similar compounds with pharmacological action have already been described in the prior art. For instance, U.S. Pat. No. 4,144,341 describes imidazopyridin-2-one derivatives for the treatment of fever and pain. WO02/30886 describes angiogenesis inhibitors which have an imidazopyridin-2-one base structure among other compounds.

Compounds with inhibitory action on endothelial lipase are described in the prior art, for example in WO2004/094394, WO2004/094393 or WO2004/093872.

It is an object of the present invention to provide alternative compounds which bring about inhibition of endothelial lipase.

SUMMARY OF THE INVENTION

The invention provides imidazopyridin-2-one derivatives of the formula I

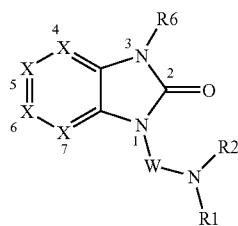

where:
X is the same or different and is =C(—R)— or =N—, where at least one X and at most two X are =N—;
W is —(C=O)—, —(S=O)—, —(SO$_2$)—;
R is the same or different and is hydrogen, halogen, (C$_1$-C$_6$)-alkyl, (C$_1$-C$_3$)-haloalkyl, (C$_1$-C$_3$)-alkyloxy-(C$_1$-C$_3$)-alkylene, aryl, heterocycle, hydroxyl, (C$_1$-C$_6$)-alkyloxy, (C$_1$-C$_3$)-haloalkyloxy, aryloxy, cyano, nitro, —S(O)$_p$—(C$_1$-C$_6$)-alkyl, where p=0, 1 or 2, aminosulfonyl, pentafluorosulfanyl, amino, (C$_1$-C$_6$)-alkylamino, di-(C$_2$-C$_{12}$)-alkylamino, (C$_1$-C$_6$)-alkylcarbonyl, COOR3, CO—NR4R5, O—CO—NR4R5, O—CO—(C$_1$-C$_6$)-alkylene-CO—O—(C$_1$-C$_6$)-alkyl, O—CO—(C$_1$-C$_6$)-alkylene-CO—OH, O—CO—(C$_1$-C$_6$)-alkylene-CO—NR4R5;
R1, R1' are the same or different and are each (C$_5$-C$_{16}$)-alkyl, (C$_5$-C$_{12}$)-cycloalkyl, (C$_1$-C$_4$)-alkylenearyl, (C$_1$-C$_4$)-alkyleneheteroaryl, (C$_1$-C$_4$)-alkylene-(C$_5$-C$_{12}$)-cycloalkyl, bicycle, where aryl, heteroaryl, cycloalkyl or bicycle may be mono- or polysubstituted preferably by halogen, (C$_1$-C$_6$)-alkyl, (C$_1$-C$_6$)-alkyloxy, hydroxyl, (C$_1$-C$_6$)-alkylmercapto, amino, (C$_1$-C$_6$)-alkylamino, di-(C$_2$-C$_{12}$)-alkylamino, mono-(C$_1$-C$_6$)-alkylaminocarbonyl, di-(C$_2$-C$_8$)-alkylaminocarbonyl, (C$_1$-C$_6$)-alkyloxycarbonyl, (C$_1$-C$_6$)-alkylcarbonyl, cyano, nitro, trifluoromethyl, trifluoromethyloxy, pentafluorosulfanyl, (C$_1$-C$_6$)-alkylsulfonyl, aminosulfonyl;
R1" is (C$_1$-C$_{16}$)-alkyl, (C$_5$-C$_{12}$)-cycloalkyl, (C$_1$-C$_4$)-alkylenearyl, (C$_1$-C$_4$)-alkyleneheteroaryl, (C$_1$-C$_4$)-alkylene-(C$_5$-C$_{12}$)-cycloalkyl, bicycle, where aryl, heteroaryl, cycloalkyl or bicycle may be mono- or polysubstituted preferably by halogen, (C$_1$-C$_6$)-alkyl, (C$_1$-C$_6$)-alkyloxy, hydroxyl, (C$_1$-C$_6$)-alkylmercapto, amino, (C$_1$-C$_6$)-alkylamino, di-(C$_2$-C$_{12}$)-alkylamino, mono-(C$_1$-C$_6$)-alkylaminocarbonyl, di-(C$_2$-C$_8$)-alkylaminocarbonyl, (C$_1$-C$_6$)-alkyloxycarbonyl, (C$_1$-C$_6$)-alkylcarbonyl, cyano, nitro, trifluoromethyl, trifluoromethyloxy, (C$_1$-C$_6$)-alkylsulfonyl, aminosulfonyl;
R2 is hydrogen;
R3 is the same or different and is hydrogen, (C$_1$-C$_6$)-alkyl, benzyl;
R4, R5 are the same or different and are each hydrogen, (C$_1$-C$_6$)-alkyl, aryl, (C$_3$-C$_{12}$)-cycloalkyl, (C$_1$-C$_4$)-alkylenearyl, (C$_1$-C$_3$)-alkylene-(C$_3$-C$_{12}$)-cycloalkyl;
R6 is hydrogen, (C$_1$-C$_{10}$)-alkyl, (C$_1$-C$_4$)-alkylenearyl, (C$_1$-C$_4$)-alkylene-heterocycle, (C$_1$-C$_4$)-alkylene-(C$_3$-C$_{12}$)-cycloalkyl, bicycle, where aryl, heterocycle, cycloalkyl or bicycle may be mono- or polysubstituted preferably by halogen, (C$_1$-C$_6$)-alkyl, (C$_1$-C$_6$)-alkyloxy, hydroxy, (C$_1$-C$_6$)-alkylmercapto, amino, (C$_1$-C$_6$)-alkylamino, di-(C$_2$-C$_{12}$)-alkylamino, mono-(C$_1$-C$_6$)-alkylaminocarbonyl, di-(C$_2$-C$_8$)-alkylaminocarbonyl, (C$_1$-C$_6$)-alkoxycarbonyl, (C$_1$-C$_6$)-alkylcarbonyl, trifluoromethyl, trifluoromethyloxy, cyano, (C$_1$-C$_6$)-alkylsulfonyl, aminosulfonyl;
or
—(C=O)—NR1'R2;
or
—(C=O)—O—R1";

with the proviso that, when R1 is (C$_5$-C$_{16}$)-alkyl, R6 is not (C$_1$-C$_4$)-alkylenearyl, (C$_1$-C$_4$)-alkylene-heterocycle, (C$_1$-C$_4$)-alkylene-(C$_3$-C$_{12}$)-cycloalkyl or bicycle;

the tautomeric forms of the compounds and their physiologically compatible salts.

DETAILED DESCRIPTION OF THE INVENTION

Preference is given to compounds of the formula I in which W is —(C=O)—.

Preference is equally given to compounds of the formula I in which
X is the same or different and is =C(—R)— or =N—, where one X is =N—.

Preference is also given to compounds of the formula I in which
X is the same or different and is =C(—R)— or =N—, where one X is =N—;
W is —(C=O)—;
R is the same or different and is hydrogen, halogen, (C$_1$-C$_6$)-alkyl, hydroxyl, phenoxy, trifluoromethyl, COOR3, pentafluorosulfanyl, amino, (C$_1$-C$_6$)-alkylamino, di-(C$_2$-C$_8$)-alkylamino, (C$_1$-C$_6$)-alkylsulfonyl, aminosulfonyl, phenyl, (C$_5$-C$_7$)-heterocycle, (C$_1$-C$_6$)-alkylcarbonyl, CO—NR4R5, O—CO—NR4R5, O—CO—(C$_1$-C$_6$)-alkylene-CO—O—(C$_1$-C$_6$)-alkyl, O—CO—(C$_1$-C$_6$)- alkylene-CO—NR4R5 or unsubstituted or mono- or poly-F-substituted $(C_1-C_3)$-alkyloxy;

R1, R1' are the same or different and are each $(C_6-C_{12})$-alkyl, $(C_1-C_3)$-alkylenearyl, $(C_1-C_3)$-alkylene-heterocycle, $(C_1-C_3)$-alkylene-$(C_5-C_{12})$-cycloalkyl, $(C_8-C_{14})$-bicycle, where aryl, heterocycle, cycloalkyl or bicycle may be mono- or polysubstituted preferably by halogen, $(C_1-C_6)$-alkyl, $(C_1-C_3)$-alkyloxy, hydroxyl, amino, $(C_1-C_6)$-alkylamino, $(C_1-C_6)$-alkyloxycarbonyl, $(C_1-C_6)$-alkylcarbonyl, cyano, trifluoromethyl, trifluoromethyloxy;

R1" is $(C_1-C_{12})$-alkyl, $(C_1-C_3)$-alkylenearyl, $(C_1-C_3)$-alkylene-heterocycle, $(C_1-C_3)$-alkylene-$(C_5-C_{12})$-cycloalkyl, $(C_8-C_{14})$-bicycle, where aryl, heterocycle, cycloalkyl or bicycle may be mono- or polysubstituted preferably by halogen, $(C_1-C_6)$-alkyl, $(C_1-C_3)$-alkyloxy, hydroxyl, amino, $(C_1-C_6)$-alkylamino, $(C_1-C_6)$-alkyloxycarbonyl, $(C_1-C_6)$-alkylcarbonyl, cyano, trifluoromethyl, trifluoromethyloxy;

R2 is hydrogen;

R3 is hydrogen, $(C_1-C_6)$-alkyl, benzyl;

R4, R5 are the same or different and are each hydrogen, $(C_1-C_6)$-alkyl, $(C_3-C_{12})$-cycloalkyl, phenyl, $(C_1-C_4)$-alkylenephenyl, $(C_1-C_4)$-alkylene-$(C_4-C_{12})$-cycloalkyl;

R6 is hydrogen, $(C_1-C_{10})$-alkyl, $(C_1-C_4)$-alkylene-phenyl, $(C_1-C_4)$-alkylene-heterocycle, $(C_1-C_4)$-alkylene-$(C_3-C_{12})$-cycloalkyl, where phenyl, heterocycle, cycloalkyl may be mono- or polysubstituted preferably by halogen, $(C_1-C_6)$-alkyl, $(C_1-C_3)$-alkyloxy, hydroxyl, $(C_1-C_6)$-alkoxycarbonyl, $(C_1-C_6)$-alkylcarbonyl, cyano, trifluoromethyl, trifluoromethyloxy, $(C_1-C_6)$-alkylsulfonyl;

or

—(C=O)—NR1'R2 or

—(C=O)—O—R1";

the tautomeric forms of the compounds and their physiologically compatible salts.

Preference is also given to the compounds of the formula I in which

X in positions 5 and 6 are identical or different and are each =C(—R)—, and in position 7 or 4 is =N—.

Further preferred compounds are those of the formula I in which

X in positions 4, 5 and 6 are identical or different and are each =C(—R)—, and in position 7 is =N—.

Particular preference is given to the compounds of the formula I in which

X is the same or different and is =C(—R)— or =N—, where one X is =N—;

W is —(C=O)—;

R is the same or different and is hydrogen, halogen, $(C_1-C_6)$-alkyl, trifluoromethyl, hydroxyl, amino, $(C_1-C_6)$-alkylcarbonyl, COOR3, $(C_1-C_6)$-alkylsulfonyl, pentafluorosulfanyl, or unsubstituted or mono- or poly-F-substituted $(C_1-C_3)$-alkyloxy;

R1, R1' are the same or different and are each $(C_6-C_{10})$-alkyl, —CH$_2$-phenyl, $(C_1-C_2)$-alkyleneheteroaryl or bicycle of the formula Ic Ic

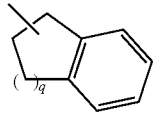

where q=1 or 2, where phenyl, heteroaryl or bicycle of the formula Ic may be mono- to disubstituted preferably by halogen, $(C_1-C_6)$-alkyl, $(C_1-C_6)$-alkyloxy, hydroxyl, amino, $(C_1-C_6)$-alkoxycarbonyl, $(C_1-C_6)$-alkylcarbonyl, cyano, trifluoromethyl, trifluoromethyloxy;

R1" is $(C_1-C_{10})$-alkyl, —CH$_2$-phenyl, $(C_1-C_2)$-alkyleneheteroaryl or bicycle of the formula Ic Ic

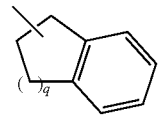

where q=1 or 2, where phenyl, heteroaryl or bicycle of the formula Ic may be mono- to disubstituted preferably by halogen, $(C_1-C_6)$-alkyl, $(C_1-C_6)$-alkyloxy, hydroxyl, amino, $(C_1-C_6)$-alkoxycarbonyl, $(C_1-C_6)$-alkylcarbonyl, cyano, trifluoromethyl, trifluoromethyloxy;

R2 is hydrogen;

R3 is hydrogen, $(C_1-C_6)$-alkyl;

R6 is hydrogen, $(C_1-C_8)$-alkyl, $(C_1-C_4)$-alkylene-phenyl, $(C_1-C_4)$-alkylene-heteroaryl, where phenyl or heteroaryl may be mono- or polysubstituted by halogen, $(C_1-C_6)$-alkyl, $(C_1-C_3)$-alkyloxy, hydroxyl, $(C_1-C_6)$-alkoxycarbonyl, $(C_1-C_6)$-alkylcarbonyl, trifluoromethyl;

or

—(C=O)—NR1'R2 or

—(C=O)—O—R1";

the tautomeric forms of the compounds and their physiologically compatible salts.

Very particular preference is given to the compounds of the formula I in which

X is the same or different and is =C(—R)— or =N—, where one X is =N—;

W is —(C=O)—;

R is the same or different and is hydrogen, halogen, hydroxyl, $(C_1-C_6)$-alkyloxy, trifluoromethyl, $(C_1-C_6)$-alkylcarbonyl or $(C_1-C_6)$-alkyl;

R1, R1' are the same or different and are each $(C_6-C_{10})$-alkyl, —CH$_2$-phenyl or bicycle of the formula Ic Ic

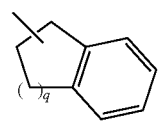

where q=1 or 2, where phenyl or bicycle may be mono- to disubstituted by halogen, $(C_1-C_6)$-alkyl, $(C_1-C_3)$-alkyloxy, $(C_1-C_6)$-alkylcarbonyl, trifluoromethyl;

R1 is $(C_1-C_{10})$-alkyl, —CH$_2$-phenyl or bicycle of the formula Ic

Ic

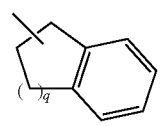

where q=1 or 2, where phenyl or bicycle may be mono- to disubstituted by halogen, $(C_1-C_6)$-alkyl, $(C_1-C_3)$-alkyloxy, $(C_1-C_6)$-alkylcarbonyl, trifluoromethyl;

R2 is hydrogen;
R6 is hydrogen, $(C_1-C_4)$-alkyl, $CH_2$-phenyl, where phenyl may be mono- or polysubstituted by halogen, $(C_1-C_6)$-alkyl, $(C_1-C_3)$-alkyloxy, hydroxyl, $(C_1-C_6)$-alkylcarbonyl, trifluoromethyl;
or
—(C=O)—NR1'R2
or
—(C=O)—O—R";

the tautomeric forms of the compounds and their physiologically compatible salts.

A particular preference is given to the compounds of the formula I in which
X is the same or different and is =C(—R)— or =N—, where one X is =N—;
W is —(C=O)—;
R is the same or different and is hydrogen, methyl;
R1, R1' are the same or different and are each $(C_6-C_{10})$-alkyl, —$CH_2$-phenyl or bicycle of the formula Id
Id

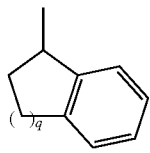

where q=1, where phenyl or bicycle may be substituted by methyl;
R2 is hydrogen;
R6 is hydrogen, methyl, or
—(C=O)—NR1'R2;

the tautomeric forms of the compound and its physiologically compatible salts.

In a further preferred embodiment of the compounds of the formula I,
W is —$(SO_2)$—.

In a further preferred embodiment of the compounds of the formula I,
R6 is hydrogen, $(C_1-C_4)$-alkyl, $(C_1-C_4)$-alkylenearyl, preferably hydrogen or $(C_1-C_4)$-alkyl, more preferably hydrogen, methyl, ethyl, n-propyl or n-butyl, most preferably hydrogen or methyl;
where aryl may be mono- or polysubstituted preferably by halogen, $(C_1-C_6)$-alkyl, $(C_1-C_6)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, trifluoromethyl, trifluoromethyloxy, cyano, $(C_1-C_6)$-alkylsulfonyl, aminosulfonyl;

with the proviso that, when R1 is $(C_5-C_{16})$-alkyl, R6 is not $(C_1-C_4)$-alkylenearyl.

In a further preferred embodiment of the compounds of the formula I,
R6 is —(C=O)—NR1'R2.

In another preferred embodiment of the compounds of the formula I,
R6 is —(C=O)—O—R1".

The invention relates to compounds of the formula I in the form of their salts, racemates, racemic mixtures and pure enantiomers, and also to their diastereomers and mixtures thereof.

The alkyl or alkylene radicals in the substituents R, R1, R1', R1", R2, R3, R4, R5 and R6 may be either straight-chain or branched. Halogen is fluorine, chlorine, bromine or iodine, particularly fluorine or chlorine.

Haloalkyl is an alkyl substituted singly, multiply or fully by halogen. Preferred halogens are fluorine and chlorine.

A cycloalkyl radical is understood to mean a ring system which comprises one or more rings and is saturated or partially unsaturated (with one or two double bonds), which is composed exclusively of carbon atoms, for example cyclopropyl, cyclopentyl, cyclopentenyl, cyclohexyl or adamantyl.

The cycloalkyl radicals may be mono- or polysubstituted by suitable groups, for example F, Cl, Br, I, $CF_3$, $NO_2$, $N_3$, CN, COOH, COO($C_1-C_6$)alkyl, $CONH_2$, CONH($C_1-C_6$)alkyl, CON[($C_1-C_6$)alkyl]$_2$, cycloalkyl, $(C_1-C_{10})$-alkyl, $(C_2-C_6)$-alkenyl, $(C_2-C_6)$-alkynyl, O—$(C_1-C_6)$-alkyl, O—CO—$(C_1-C_6)$-alkyl, O—CO—$(C_1-C_6)$-aryl, O—CO—$(C_1-C_6)$-heterocycle; $PO_3H_2$, $SO_3H$, $SO_2$—$NH_2$, $SO_2NH(C_1-C_6)$-alkyl, $SO_2N[(C_1-C_6)$-alkyl]$_2$, S—$(C_1-C_6)$-alkyl, S—$(CH_2)_n$-aryl, S—$(CH_2)_n$-heterocycle, SO—$(C_1-C_6)$-alkyl, SO—$(CH_2)_n$-aryl, SO—$(CH_2)_n$-heterocycle, $SO_2$—$(C_1-C_6)$-alkyl, $SO_2$—$(CH_2)_n$-aryl, $SO_2$—$(CH_2)_n$-heterocycle, $SO_2$—NH$(CH_2)_n$-aryl, $SO_2$—NH$(CH_2)_n$-heterocycle, $SO_2$—N$((C_1-C_6)$-alkyl)$(CH_2)_n$-aryl, $SO_2$—N$((C_1-C_6)$-alkyl)$(CH_2)_n$-heterocycle, $SO_2$—N$((CH_2)_n$-aryl)$_2$, $SO_2$—N$((CH_2)_n$-heterocycle)$_2$ where n may be 0-6 and the aryl radical or heterocyclic radical may be up to disubstituted by F, Cl, Br, OH, $CF_3$, $NO_2$, CN, $OCF_3$, O—$(C_1-C_6)$-alkyl, $(C_1-C_6)$-alkyl, $NH_2$; C(NH)($NH_2$), $NH_2$, NH—$(C_1-C_6)$-alkyl, N$((C_1-C_6)$-alkyl)$_2$, NH($C_1-C_7$)-acyl, NH—CO—$(C_1-C_6)$-alkyl, NH—COO—$(C_1-C_6)$-alkyl, NH—CO-aryl, NH—CO-heterocycle, NH—COO-aryl, NH—COO-heterocycle, NH—CO—NH—$(C_1-C_6)$-alkyl, NH—CO—NH-aryl, NH—CO—NH-heterocycle, N$(C_1-C_6)$-alkyl —CO—$(C_1-C_6)$-alkyl, N$(C_1-C_6)$-alkyl —COO—$(C_1-C_6)$-alkyl, N$(C_1-C_6)$-alkyl —CO-aryl, N$(C_1-C_6)$-alkyl —CO-heterocycle, N$(C_1-C_6)$-alkyl —COO-aryl, N$(C_1-C_6)$-alkyl —COO-heterocycle, N$(C_1-C_6)$-alkyl —CO—NH—$(C_1-C_6)$-alkyl, N$(C_1-C_6)$-alkyl —CO—NH-aryl, N$(C_1-C_6)$-alkyl —CO—NH-heterocycle, N$((C_1-C_6)$-alkyl)-CO—N—$((C_1-C_6)$-alkyl)$_2$, N$((C_1-C_6)$-alkyl)-CO—N$((C_1-C_6)$-alkyl)-aryl, N$((C_1-C_6)$-alkyl)-CO—N$((C_1-C_6)$-alkyl)-heterocycle, N$((C_1-C_6)$-alkyl)-CO—N-(aryl)$_2$, N$((C_1-C_6)$-alkyl)-CO—N-(heterocycle)$_2$, N(aryl)-CO—$(C_1-C_6)$-alkyl, N(heterocycle)-CO—$(C_1-C_6)$-alkyl, N(aryl)-COO—$(C_1-C_6)$-alkyl, N(heterocycle)-COO—$(C_1-C_6)$-alkyl, N(aryl)-CO-aryl, N(heterocycle)-CO-aryl, N(aryl)-COO-aryl, N(heterocycle)-COO-aryl, N(aryl)-CO—NH—$(C_1-C_6)$-alkyl, N(heterocycle)-CO—NH—$(C_1-C_6)$-alkyl, N(aryl)-CO—NH-aryl, N(heterocycle)-CO—NH-aryl, N(aryl)-CO—N—$((C_1-C_6)$-alkyl)$_2$, N(heterocycle)-CO—N—$((C_1-C_6)$-alkyl)$_2$, N(aryl)-CO—N$((C_1-C_6)$-alkyl)-aryl, N(heterocycle)-CO—N$((C_1-C_6)$-alkyl)-aryl, N(aryl)-CO—N-(aryl)$_2$, N(heterocycle)-CO—N-(aryl)$_2$, aryl, O—$(CH_2)_n$-aryl, O—$(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, O—$(C_1-C_6)$-alkyl, $(C_1-C_6)$-alkyl, $NH_2$, NH($C_1-C_6)$-alkyl, N$((C_1-C_6)$-alkyl)$_2$, $SO_2$—$CH_3$, COOH, COO—$(C_1-C_6)$-alkyl, $CONH_2$.

Bicycle is a partly unsaturated bicyclic ring system which has from 8 to 14 ring members and has exclusively carbon atoms as ring members. Ring systems which contain a fused benzene ring are included in this definition. Mention is made by way of example of the tetrahydronaphthyl, alpha- or beta-tetralonyl, indanyl or indan-1-onyl radical. Preferred bicycle radicals are tetrahydronaphthyl and indanyl.

The bicycle radicals may be mono- or polysubstituted by suitable groups, for example: F, Cl, Br, I, $CF_3$, $NO_2$, $N_3$, CN, COOH, $COO(C_1-C_6)$alkyl, $CONH_2$, $CONH(C_1-C_6)$alkyl, $CON[(C_1-C_6)$alkyl$]_2$, cycloalkyl, $(C_1-C_{10})$-alkyl, $(C_2-C_6)$-alkenyl, $(C_2-C_6)$-alkynyl, $O-(C_1-C_6)$-alkyl, $O-CO-(C_1-C_6)$-alkyl, $O-CO-(C_1-C_6)$-aryl, $O-CO-(C_1-C_6)$-heterocycle; $PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N(C_1-C_6)$-alkyl)$(CH_2)_n$-aryl, $SO_2-N((C_1-C_6)$-alkyl)$(CH_2)_n$-heterocycle, $SO_2-N((CH_2)_n$-aryl$)_2$, $SO_2-N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, $O-(C_1-C_6)$-alkyl, $(C_1-C_6)$-alkyl, $NH_2$;

$C(NH)(NH_2)$, $NH_2$, $NH-(C_1-C_6)$-alkyl, $N((C_1-C_6)$-alkyl$)_2$, $NH(C_1-C_7)$-Acyl, $NH-CO-(C_1-C_6)$-alkyl, $NH-COO-(C_1-C_6)$-alkyl, $NH-CO$-aryl, $NH-CO$-heterocycle, $NH-COO$-aryl, $NH-COO$-heterocycle, $NH-CO-NH-(C_1-C_6)$-alkyl, $NH-CO-NH$-aryl, $NH-CO-NH$-heterocycle, $N(C_1-C_6)$-alkyl $-CO-(C_1-C_6)$-alkyl, $N(C_1-C_6)$-alkyl $-COO-(C_1-C_6)$-alkyl, $N(C_1-C_6)$-alkyl $-CO$-aryl, $N(C_1-C_6)$-alkyl $-CO$-heterocycle, $N(C_1-C_6)$-alkyl $-COO$-aryl, $N(C_1-C_6)$-alkyl $-COO$-heterocycle, $N(C_1-C_6)$-alkyl $-CO-NH-(C_1-C_6)$-alkyl, $N(C_1-C_6)$-alkyl $-CO-NH$-aryl, $N(C_1-C_6)$-alkyl $-CO-NH$-heterocycle, $N((C_1-C_6)$-alkyl)$-CO-N-((C_1-C_6)$-alkyl$)_2$, $N((C_1-C_6)$-alkyl)$-CO-N((C_1-C_6)$-alkyl)-aryl, $N((C_1-C_6)$-alkyl)$-CO-N((C_1-C_6)$-alkyl)-heterocycle, $N((C_1-C_6)$-alkyl)$-CO-N$-(aryl$)_2$, $N((C_1-C_6)$-alkyl)$-CO-N$-(heterocycle$)_2$, $N($aryl$)-CO-(C_1-C_6)$-alkyl, $N($heterocycle$)-CO-(C_1-C_6)$-alkyl, $N($aryl$)-COO-(C_1-C_6)$-alkyl, $N($heterocycle$)-COO-(C_1-C_6)$-alkyl, $N($aryl$)-CO$-aryl, $N($heterocycle$)-CO$-aryl, $N($aryl$)-COO$-aryl, $N($heterocycle$)-COO$-aryl, $N($aryl$)-CO-NH-(C_1-C_6)$-alkyl, $N($heterocycle$)-CO-NH-(C_1-C_6)$-alkyl, $N($aryl$)-CO-NH$-aryl, $N($heterocycle$)-CO-NH$-aryl, $N($aryl$)-CO-N-((C_1-C_6)$-alkyl$)_2$, $N($heterocycle$)-CO-N-((C_1-C_6)$-alkyl$)_2$, $N($aryl$)-CO-N((C_1-C_6)$-alkyl)-aryl, $N($heterocycle$)-CO-N((C_1-C_6)$-alkyl)-aryl, $N($aryl$)-CO-N$-(aryl$)_2$, $N($heterocycle$)-CO-N$-(aryl$)_2$, aryl, $O-(CH_2)_n$-aryl, $O-(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, $CONH_2$.

An aryl radical is understood to mean a phenyl or naphthyl radical.

The aryl radicals may be mono- or polysubstituted by suitable groups, for example: F, Cl, Br, I, $CF_3$, $NO_2$, CN, COOH, $COO(C_1-C_6)$alkyl, $CONH_2$, $CONH(C_1-C_6)$alkyl, $CON[(C_1-C_6)$alkyl$]_2$, $(C_3-C_{10})$-cycloalkyl, $(C_1-C_1-C_{10})$-alkyl, $(C_2-C_6)$-alkenyl, $(C_2-C_6)$-alkynyl, $O-(C_1-C_6)$-alkyl, $O-CO-(C_1-C_6)$-alkyl, $O-CO-(C_1-C_6)$-aryl, $PO_3H_2$, $SO_3H$, $SO_2-NH_2$, $SO_2NH(C_1-C_6)$-alkyl, $SO_2N[(C_1-C_6)$-alkyl$]_2$, $S-(C_1-C_6)$-alkyl, $S-(CH_2)_n$-aryl, $S-(CH_2)_n$-heterocycle, $SO-(C_1-C_6)$-alkyl, $SO-(CH_2)_n$-aryl, $SO-(CH_2)_n$-heterocycle, $SO_2-(C_1-C_6)$-alkyl, $SO_2-(CH_2)_n$-aryl, $SO_2-(CH_2)_n$-heterocycle, $SO_2-NH(CH_2)_n$-aryl, $SO_2-NH(CH_2)_n$-heterocycle, $SO_2-N((C_1-C_6)$-alkyl)$(CH_2)_n$-aryl, $SO_2-N((C_1-C_6)$-alkyl)$(CH_2)_n$-heterocycle, $SO_2-N((CH_2)_n$-aryl$)_2$, $SO_2-N((CH_2)_n$-heterocycle$)_2$ where n may be 0-6 and the aryl radical or heterocyclic radical may be up to disubstituted by F, Cl, Br, OH, $CF_3$, $NO_2$, CN, $OCF_3$, $O-(C_1-C_6)$-alkyl, $(C_1-C_6)$-alkyl, $NH_2$; $C(NH)(NH_2)$, $NH_2$, $NH-(C_1-C_6)$-alkyl, $N((C_1-C_6)$-alkyl$)_2$, $NH(C_1-C_7)$-Acyl, $NH-CO-(C_1-C_6)$-alkyl, $NH-COO-(C_1-C_6)$-alkyl, $NH-CO$-aryl, $NH-CO$-heterocycle, $NH-COO$-aryl, $NH-COO$-heterocycle, $NH-CO-NH-(C_1-C_6)$-alkyl, $NH-CO-NH$-aryl, $NH-CO-NH$-heterocycle, $N(C_1-C_6)$-alkyl $-CO-(C_1-C_6)$-alkyl, $N(C_1-C_6)$-alkyl $-COO-(C_1-C_6)$-alkyl, $N(C_1-C_6)$-alkyl $-CO$-aryl, $N(C_1-C_6)$-alkyl $-CO$-heterocycle, $N(C_1-C_6)$-alkyl $-COO$-aryl, $N(C_1-C_6)$-alkyl $-COO$-heterocycle, $N(C_1-C_6)$-alkyl $-CO-NH-(C_1-C_6)$-alkyl, $N(C_1-C_6)$-alkyl $-CO-NH$-aryl, $N(C_1-C_6)$-alkyl $-CO-NH$-heterocycle, $N((C_1-C_6)$-alkyl)$-CO-N-((C_1-C_6)$-alkyl$)_2$, $N((C_1-C_6)$-alkyl)$-CO-N((C_1-C_6)$-alkyl)-aryl, $N((C_1-C_6)$-alkyl)$-CO-N((C_1-C_6)$-alkyl)-heterocycle, $N((C_1-C_6)$-alkyl)$-CO-N$-(aryl$)_2$, $N((C_1-C_6)$-alkyl)$-CO-N$-(heterocycle$)_2$, $N($aryl$)-CO-(C_1-C_6)$-alkyl, $N($heterocycle$)-CO-(C_1-C_6)$-alkyl, $N($aryl$)-COO-(C_1-C_6)$-alkyl, $N($heterocycle$)-COO-(C_1-C_6)$-alkyl, $N($aryl$)-CO$-aryl, $N($heterocycle$)-CO$-aryl, $N($aryl$)-COO$-aryl, $N($heterocycle$)-COO$-aryl, $N($aryl$)-CO-NH-(C_1-C_6)$-alkyl, $N($heterocycle$)-CO-NH-(C_1-C_6)$-alkyl, $N($aryl$)-CO-NH$-aryl, $N($heterocycle$)-CO-NH$-aryl, $N($aryl$)-CO-N-((C_1-C_6)$-alkyl$)_2$, $N($heterocycle$)-CO-N-((C_1-C_6)$-alkyl$)_2$, $N($aryl$)-CO-N((C_1-C_6)$-alkyl)-aryl, $N($heterocycle$)-CO-N((C_1-C_6)$-alkyl)-aryl, $N($aryl$)-CO-N$-(aryl$)_2$, $N($heterocycle$)-CO-N$-(aryl$)_2$, aryl, $O-(CH_2)_n$-aryl, $O-(CH_2)_n$-heterocycle, where n may be 0-6, where the aryl radical or heterocyclic radical may be mono- to trisubstituted by F, Cl, Br, I, OH, $CF_3$, $NO_2$, CN, $OCF_3$, $O-(C_1-C_6)$-alkyl, $(C_1-C_6)$-alkyl, $NH_2$, $NH(C_1-C_6)$-alkyl, $N((C_1-C_6)$-alkyl$)_2$, $SO_2-CH_3$, COOH, $COO-(C_1-C_6)$-alkyl, $CONH_2$.

Heterocycle is a mono- or bicyclic ring system having from 5 to 12 ring members, in which at least one atom in the ring system is a heteroatom selected from the group consisting of N, O and S. This definition also includes ring systems in which the heterocycle is fused to a benzene ring. $(C_5-C_7)$-Heterocycle is a monocyclic ring system; $(C_8-C_{12})$-heterocycle is a bicyclic ring system.

Suitable "heterocyclic rings" or "heterocyclic radicals" are azocinyl, benzimidazolyl, benzofuryl, benzothienyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, 2H,6H-1,5,2-dithiazinyl, dihydrofuro[2,3-b]tetrahydrofuryl, furyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, 6H-1,2,5-thiadiazinyl, thiazolyl, 1,2,3-thiadiazolyl, 1,2,4-thiadiazolyl, 1,2,5-thiadiazolyl, 1,3,4-thiadiazolyl, thienyl, triazolyl, tetrazolyl and xanthenyl.

Pyridyl is any of 2-, 3- or 4-pyridyl. Thienyl is either 2- or 3-thienyl. Furyl is either 2- or 3-furyl.

Also included are the corresponding N-oxides of these compounds, for example 1-oxy-2-, -3- or -4-pyridyl.

The heterocyclic rings or heterocyclic radicals may be mono- or polysubstituted by suitable groups, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, where one, more than one or all hydrogen(s) in the alkyl radicals may be replaced by fluorine; $PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl, where n may be 0-6 and the phenyl radical may be up to disubstituted by F, Cl, Br, OH, $CF_3$, $NO_2$, CN, $OCF_3$, O—($C_1$-$C_6$)-alkyl, ($C_1$-$C_6$)-alkyl, $NH_2$; C(NH)(NH$_2$), $NH_2$, NH—($C_1$-$C_6$)-alkyl, N(($C_1$-$C_6$)-alkyl)$_2$, NH($C_1$-$C_7$)-acyl, phenyl, O—$(CH_2)_n$-phenyl where n may be 0-6, where the phenyl ring may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Heteroaryl is a mono- or bicyclic aromatic ring system having from 5 to 12 ring members, in which at least one atom in the ring system is a heteroatom selected from the group consisting of N, O and S. This definition also includes ring systems in which the heteroaryl is fused to a benzene ring.

Suitable "heteroaryl rings" or "heteroaryl radicals" are, for example, benzimidazolyl, benzofuranyl, benzothiophenyl, benzoxazolyl, benzthiazolyl, benztriazolyl, benztetrazolyl, benzisoxazolyl, benzisothiazolyl, quinolinyl, furyl, furazanyl, imidazolyl, 1H-indazolyl, indolyl, 1,2,3-oxadiazolyl, 1,2,4-oxadiazolyl, 1,2,5-oxadiazolyl, 1,3,4-oxadiazolyl, pyrimidinyl, pyrazinyl, pyrazolyl, pyridyl, pyrrolyl, thiazolyl, 1,2,3-thiadiazolyl, 1,2,4-thiadiazolyl, 1,2,5-thiadiazolyl, 1,3,4-thiadiazolyl, thiophenyl. Preferred heteroaryl radicals are benzothiophenyl and thiophenyl.

The heteroaryl rings or heteroaryl radicals may be mono- or polysubstituted by suitable groups, for example: F, Cl, Br, I, $CF_3$, $NO_2$, $N_3$, CN, COOH, COO($C_1$-$C_6$)alkyl, $CONH_2$, CONH($C_1$-$C_6$)alkyl, CON[($C_1$-$C_6$)alkyl]$_2$, ($C_1$-$C_6$)-alkyl, ($C_2$-$C_6$)-alkenyl, ($C_2$-$C_6$)-alkynyl, O—($C_1$-$C_6$)-alkyl, where one, more than one or all hydrogen(s) in the alkyl radicals may be replaced by fluorine; $PO_3H_2$, $SO_3H$, $SO_2$—$NH_2$, $SO_2NH(C_1$-$C_6)$-alkyl, $SO_2N[(C_1$-$C_6)$-alkyl]$_2$, S—($C_1$-$C_6$)-alkyl, S—$(CH_2)_n$-phenyl, SO—($C_1$-$C_6$)-alkyl, SO—$(CH_2)_n$-phenyl, $SO_2$—($C_1$-$C_6$)-alkyl, $SO_2$—$(CH_2)_n$-phenyl where n may be 0-6 and the phenyl radical may be up to disubstituted by F, Cl, Br, OH, $CF_3$, $NO_2$, CN, $OCF_3$, O—($C_1$-$C_6$)-alkyl, ($C_1$-$C_6$)-alkyl, $NH_2$; C(NH)(NH$_2$), $NH_2$, NH—($C_1$-$C_6$)-alkyl, N(($C_1$-$C_6$)-alkyl)$_2$, NH($C_1$-$C_7$)-acyl, phenyl, O—$(CH_2)_n$-phenyl, where n may be 0-6, where the phenyl ring may be mono- to trisubstituted by F, Cl, Br, I, OH, $CF_3$, $NO_2$, CN, $OCF_3$, O—($C_1$-$C_6$)-alkyl, ($C_1$-$C_6$)-alkyl, $NH_2$, NH($C_1$-$C_6$)-alkyl, N(($C_1$-$C_6$)-alkyl)$_2$, $SO_2$—$CH_3$, COOH, COO—($C_1$-$C_6$)-alkyl, $CONH_2$.

Owing to their higher water solubility, pharmaceutically acceptable salts are particularly suitable for medical applications compared to the starting or base compounds. These salts must have a pharmaceutically acceptable anion or cation. Suitable pharmaceutically acceptable acid addition salts of the inventive compounds are salts of inorganic acids such as hydrochloric acid, hydrobromic acid, phosphoric acid, metaphosphoric acid, nitric acid and sulfuric acid, and organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid and tartaric acid. Suitable pharmaceutically acceptable basic salts are ammonium salts, alkali metal salts (such as sodium and potassium salts) and alkaline earth metal salts (such as magnesium and calcium salts) and salts of trometamol (2-amino-2-hydroxymethyl-1, 3-propanediol), diethanolamine, lysine or ethylenediamine.

Salts with a pharmaceutically unacceptable anion, for example trifluoroacetate, are likewise included in the scope of the invention as useful intermediates for the preparation or purification of pharmaceutically acceptable salts and/or for the use in non-therapeutic, for example in vitro, applications.

The term "physiologically functional derivative" used here refers to any physiologically compatible derivative of an inventive compound of the formula I, for example an ester which, on administration to a mammal, for example the human, is capable (directly or indirectly) of forming a compound of the formula I or an active metabolite thereof.

The physiologically functional derivatives also include prodrugs of the inventive compounds, as described, for example, in H. Okada et al., Chem. Pharm. Bull., 1994, 42, 57-61. Such prodrugs can be metabolized in vivo to give an inventive compound. These prodrugs may themselves be active or not.

The inventive compounds may also be present in various polymorphic forms, for example as amorphous and crystalline polymorphic forms. All polymorphic forms of the inventive compounds are included within the scope of the invention and are a further aspect of the invention.

Hereinafter, all references to "compound(s) of the formula I" relate to compound(s) of the formula I as described above, and also their salts, solvates and physiologically functional derivatives as described herein.

Use

The compounds of the formula I in which

X is the same or different and is =C(—R)— or =N—, where at least one X and at most two X are =N—;

W is —(C=O)—, —(S=O)—, —(SO$_2$)—;

R is the same or different and is hydrogen, halogen, ($C_1$-$C_6$)-alkyl, ($C_1$-$C_3$)-haloalkyl, ($C_1$-$C_3$)-alkyloxy-($C_1$-$C_3$)-alkylene, aryl, heterocycle, hydroxyl, ($C_1$-$C_6$)-alkyloxy, ($C_1$-$C_3$)-haloalkyloxy, aryloxy, cyano, nitro, —S(O)$_p$—($C_1$-$C_6$)-alkyl, where p=0, 1 or 2, aminosulfonyl, pentafluorosulfanyl, amino, ($C_1$-$C_6$)-alkylamino, di-($C_2$-$C_{12}$)-alkylamino, ($C_1$-$C_6$)-alkylcarbonyl, COOR3, CO—NR4R5, O—CO—NR4R5, O—CO—($C_1$-$C_6$)-alkylene-CO—O—($C_1$-$C_6$)-alkyl, O—CO—($C_1$-$C_6$)-alkylene-CO—OH, O—CO—($C_1$-$C_6$)-alkylene-CO—NR4R5;

R1, R1' are the same or different and are each ($C_5$-$C_{16}$)-alkyl, ($C_5$-$C_{12}$)-cycloalkyl, ($C_1$-$C_4$)-alkylenearyl, ($C_1$-$C_4$)-alkyleneheteroaryl, ($C_1$-$C_4$)-alkylene-($C_5$-$C_{12}$)-cycloalkyl, bicycle, where aryl, heteroaryl, cycloalkyl or bicycle may be mono- or polysubstituted preferably by halogen, ($C_1$-$C_6$)-alkyl, ($C_1$-$C_6$)-alkyloxy, hydroxyl, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)-alkyloxycarbonyl, ($C_1$-$C_6$)-alkylcarbonyl, cyano, nitro, trifluoromethyl, trifluoromethyloxy, pentafluorosulfanyl, ($C_1$-$C_6$)-alkylsulfonyl, aminosulfonyl;

R1" is ($C_1$-$C_{16}$)-alkyl, ($C_5$-$C_{12}$)-cycloalkyl, ($C_1$-$C_4$)-alkylenearyl, ($C_1$-$C_4$)-alkyleneheteroaryl, ($C_1$-$C_4$)-alkylene-($C_5$-$C_{12}$)-cycloalkyl, bicycle, where aryl, heteroaryl, cycloalkyl or bicycle may be mono- or polysubstituted preferably by halogen, ($C_1$-$C_6$)-alkyl, ($C_1$-$C_6$)-alkyloxy, hydroxyl, ($C_1$-$C_6$)-alkylmercapto, amino, ($C_1$-$C_6$)-alkylamino, di-($C_2$-$C_{12}$)-alkylamino, mono-($C_1$-$C_6$)-alkylaminocarbonyl, di-($C_2$-$C_8$)-alkylaminocarbonyl, ($C_1$-$C_6$)- alkyloxycarbonyl, $(C_1-C_6)$-alkylcarbonyl, cyano, nitro, trifluoromethyl, trifluoromethyloxy, $(C_1-C_6)$-alkylsulfonyl, aminosulfonyl;

R2 is hydrogen;

R3 is the same or different and is hydrogen, $(C_1-C_6)$-alkyl, benzyl;

R4, R5 are the same or different and are each hydrogen, $(C_1-C_6)$-alkyl, aryl, $(C_3-C_{12})$-cycloalkyl, $(C_1-C_4)$-alkylenearyl, $(C_1-C_3)$-alkylene-$(C_3-C_{12})$-cycloalkyl;

R6 is hydrogen, $(C_1-C_{10})$-alkyl, $(C_1-C_4)$-alkylenearyl, $(C_1-C_4)$-alkylene-heterocycle, $(C_1-C_4)$-alkylene-$(C_3-C_{12})$-cycloalkyl, $(C_8-C_{14})$-bicycle, where aryl, heterocycle, cycloalkyl or bicycle may be mono- or polysubstituted preferably by halogen, $(C_1-C_6)$-alkyl, $(C_1-C_6)$-alkyloxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkoxycarbonyl, $(C_1-C_6)$-alkylcarbonyl, trifluoromethyl, trifluoromethyloxy, cyano, $(C_1-C_6)$-alkylsulfonyl, aminosulfonyl;

or

—(C=O)—NR1'R2;

or

—(C=O)—NH$_2$;

or

—(C=O)—O—R1";

and the tautomeric forms of the compounds and also their physiologically compatible salts have a surprising inhibitory effect on endothelial lipase (EL). HDL, which has antiatherosclerotic action, is the preferred substrate for EL. A lowering of the HDL level leads to the progression of atherosclerosis and its sequelae such as coronary heart disease and additionally promotes the development of metabolic syndrome and its sequela of diabetes. An inhibition of the EL should thus lead generally to the prevention of atherosclerotic disorders and indirectly reduce the probability of illness in persons with an increased risk of diabetes.

It has also been found that the inhibitory effect of the inventive compounds of the formula I is selective compared to other lipases.

The compounds of the formula I are notable for exhibiting an improved solubility compared with compounds of similar structure in aqueous media with at least the same time high activity. Preferred compounds of the invention further exhibit an improved metabolic stability compared with compounds of the prior art.

Furthermore the compounds of the invention show advantages in terms of serum stability.

Such compounds are particularly suitable for the treatment and/or prevention of

1. Dyslipidemias and general impairments of lipid metabolism and their sequelae, for example atherosclerosis, coronary heart disease, cerebrovascular disorders etc., especially those (but not restricted thereto) which are characterized by one or more of the following factors:
   high plasma triglyceride concentrations, high postprandial plasma triglyceride concentrations,
   low HDL cholesterol concentration
   low ApoA lipoprotein concentrations
   high LDL cholesterol concentrations
   small dense LDL cholesterol particles
   high ApoB lipoprotein concentrations
2. Various other conditions which may be associated with the metabolic syndrome, such as:
   obesity (excess weight), including central obesity
   thromboses, hypercoagulable and prothrombotic stages (arterial and venous)
   high blood pressure
   heart failure, for example (but not restricted thereto) following myocardial infarction, hypertensive heart disease or cardiomyopathy
   diabetes mellitus, in particular type 2 diabetes, including the prevention of the sequelae associated therewith (hyperglycemia, glucose intolerance, loss of pancreatic β cells, macro- and microvascular disorders
3. Other disorders or conditions in which inflammatory reactions or cell differentiation, for example, are involved are:
   atherosclerosis, for example (but not restricted thereto) coronary sclerosis, including angina pectoris or myocardial infarction, stroke
   vascular restenosis or reocclusion
   chronic inflammatory bowel diseases, for example Crohn's disease and ulcerative colitis
   pancreatitis
   other inflammatory states
   retinopathy
   adipose cell tumors
   adipose cell carcinomas, for example liposarcomas
   solid tumors and neoplasms, for example (but not restricted thereto) carcinomas of the gastrointestinal tract, of the liver, of the biliary tract and of the pancreas, endocrine tumors, carcinomas of the lungs, of the kidney and the urinary tract, of the genital tract, prostate carcinomas, etc.
   acute and chronic myeloproliferative disorders and lymphomas
   angiogenesis
   neurodegenerative disorders
   Alzheimer's disease
   multiple sclerosis
   Parkinson's disease
   erythemato-squamous dermatoses, for example psoriasis
   acne vulgaris
   other skin disorders and dermatological conditions which are modulated by PPAR
   eczemas and neurodermatitis
   dermatitis for example seborrheic dermatitis or photodermatitis
   keratitis and keratoses, for example seborrheic keratoses, senile keratoses, actinic keratosis, photo-induced keratoses or keratosis follicularis
   keloids and keloid prophylaxis
   warts, including condylomata or condylomata acuminata
   human papilloma viral (HPV) infections, for example venereal papillomata, viral warts, for example molluscum contagiosum, leukoplakia
   papular dermatoses, for example lichen planus
   skin cancer, for example basal-cell carcinomas, melanomas or cutaneous T-cell lymphomas
   localized benign epidermal tumors, for example keratoderma, epidermal naevi
   chilblains
   high blood pressure
   syndrome X
   polycystic ovary syndrome (PCOS)
   asthma
   osteoarthritis
   lupus erythematosus (LE) or inflammatory rheumatic disorders, for example rheumatoid arthritis
   vasculitis
   wasting (cachexia)
   gout
   ischemia/reperfusion syndrome
   acute respiratory distress syndrome (ARDS) ("shock lung").

Formulation

The amount of an inventive compound which is required in order to achieve the desired biological effect is dependent upon a series of factors, for example the specific compound selected, the intended use, the mode of administration and the clinical condition of the patient. The daily dose is generally in the range from 0.3 mg to 100 mg (typically from 3 mg to 50 mg) per day per kilogram of bodyweight, for example 3-10 mg/kg/day. An intravenous dose may, for example, be in the range from 0.3 mg to 1.0 mg/kg and may suitably be administered as an infusion of from 10 ng to 100 ng per kilogram per minute. Suitable infusion solutions for these purposes may, for example, contain from 0.1 ng to 10 mg, typically from 1 ng to 10 mg, per milliliter. Single doses may contain, for example, from 1 mg to 10 g of the active ingredient. Ampoules for injections may therefore contain, for example, from 1 mg to 100 mg, and single dose formulations which can be administered orally, for example tablets or capsules, may contain, for example, from 0.05 to 1000 mg, typically from 0.5 to 600 mg. The compounds of the formula I may be used for therapy of the abovementioned conditions as the compounds themselves, although they are preferably in the form of a pharmaceutical composition with an acceptable carrier. The carrier of course has to be acceptable, in the sense that it is compatible with the other constituents of the composition and is not damaging to the health of the patient. The carrier may be a solid or a liquid or both and is preferably formulated with the compound as a single dose, for example as a tablet, which may contain from 0.05 to 95% by weight of the active ingredient. Further pharmaceutically active substances may likewise be present, including further inventive compounds. The inventive pharmaceutical compositions may be produced by one of the known pharmaceutical methods which consist essentially in mixing the constituents with pharmacologically acceptable carriers and/or excipients.

Inventive pharmaceutical compositions are those which are suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the type of the compound of formula I used in each case. Coated formulations and coated slow-release formulations are also encompassed by the scope of the invention. Preference is given to acid- and gastric fluid-resistant formulations. Suitable gastric fluid-resistant coatings include cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units, for example capsules, cachets, lozenges or tablets, each of which contains a certain amount of the compound of the formula I; as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional constituents) are brought into contact. In general, the compositions are prepared by uniform and homogeneous mixing of the active ingredient with a liquid carrier and/or finely divided solid carrier, after which the product is shaped if necessary. For example, a tablet can thus be produced by compressing or shaping a powder or granules of the compound, optionally with one or more additional constituents. Compressed tablets can be prepared by tableting the compound in free-flowing form, for example a powder or granules, optionally mixed with a binder, lubricant, inert diluent and/or one (or more) surfactants/dispersants in a suitable machine. Shaped tablets can be prepared by shaping the pulverulent compound moistened with an inert liquid diluent in a suitable machine.

Pharmaceutical compositions which are suitable for peroral (sublingual) administration include lozenges which contain a compound of formula I with a flavoring, customarily sucrose, and gum arabic or tragacanth, and pastilles which include the compound in an inert base, such as gelatin and glycerol or sucrose and gum arabic.

Suitable pharmaceutical compositions for parenteral administration include preferably sterile aqueous preparations of a compound of the formula I which are preferably isotonic with the blood of the intended recipient. These preparations are preferably administered intravenously, although the administration may also be subcutaneous, intramuscular or intradermal as an injection. These preparations can preferably be produced by mixing the compound with water and making the solution obtained sterile and isotonic with the blood. Injectable compositions according to the invention generally contain from 0.1 to 5% by weight of the active compound.

Suitable pharmaceutical compositions for rectal administration are preferably in the form of single dose suppositories. These can be prepared by mixing a compound of the formula I with one or more conventional solid carriers, for example cocoa butter, and shaping the resulting mixture.

Suitable pharmaceutical compositions for topical application on the skin are preferably in the form of an ointment, cream, lotion, paste, spray, aerosol or oil. Useful carriers include petroleum jelly, lanolin, polyethylene glycols, alcohols and combinations of two or more of these substances. The active ingredient is generally present in a concentration of from 0.1 to 15% by weight of the composition, preferably from 0.5 to 2%.

Transdermal administration is also possible. Suitable pharmaceutical compositions for transdermal applications may be in the form of single plasters which are suitable for long-term close contact with the epidermis of the patient. Such plasters suitably contain the active ingredient in an optionally buffered aqueous solution, dissolved and/or dispersed in an adhesive or dispersed in a polymer. A suitable active ingredient concentration is from approx. 1% to 35%, preferably from approx. 3% to 15%. A particular means of releasing the active ingredient may be by electrotransport or iontophoresis, as described, for example, in Pharmaceutical Research, 2(6): 318 (1986).

The compounds of the formula I are notable for favorable effects on disorders of lipid metabolism. They positively influence the HDL to LDL ratio and increase in particular the HDL level and are suitable for the prevention and treatment of dyslipidemias and metabolic syndrome and their diverse sequelae such as atherosclerosis, coronary heart disease, heart failure, obesity and diabetes.

Combinations with Other Medicaments

The compounds of the invention can be administered alone or in combination with one or more further pharmacologically active ingredients. In particular, the compounds of the invention can be administered with active ingredients which have a similar pharmacological effect to themselves. For example, they can be administered in combination with active ingredients which have favorable effects on metabolic disturbances or disorders frequently associated therewith. Examples of such medicaments are
   1. medicaments which lower blood glucose, antidiabetics,
   2. active ingredients for the treatment of dyslipidemias,
   3. antiatherosclerotic medicaments,
   4. antiobesity agents,
   5. antiinflammatory active ingredients
   6. active ingredients for the treatment of malignant tumors
   7. antithrombotic active ingredients 8. active ingredients for the treatment of high blood pressure
9. active ingredients for the treatment of heart failure and
10. active ingredients for the treatment and/or prevention of complications caused by diabetes or associated with diabetes
11. active ingredients for the treatment of neurodegenerative diseases
12. active ingredients for the treatment of diseases of the central nervous system
13. active ingredients for the treatment of dependence on drugs, nicotine and alcohol
14. analgesics They can be combined with the compounds of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation.

Further active ingredients particularly suitable for the combination products are:

All antidiabetics which are mentioned in the Rote Liste 2006, chapter 12; all weight-reducing agents/appetite suppressants which are mentioned in the Rote Liste 2006, chapter 1; all lipid-lowering agents which are mentioned in the Rote Liste 2006, chapter 58. They can be combined with the compound of the invention of the formula I in particular for a synergistic improvement in the effect. Administration of the active ingredient combination can take place either by separate administration of the active ingredients to the patient or in the form of combination products in which a plurality of active ingredients are present in one pharmaceutical preparation. Most of the active ingredients mentioned hereinafter are disclosed in the USP Dictionary of USAN and International Drug Names, US Pharmacopeia, Rockville 2001.

Antidiabetics include insulin and insulin derivatives such as, for example, Lantus® (see www.lantus.com) or HMR 1964 or those described in WO 2005/005477 (Novo Nordisk), fast-acting insulins (see U.S. Pat. No. 6,221,633), inhalable insulins such as, for example, Exubera® or oral insulins such as, for example, IN-105 (Nobex) or Oral-lyn™ (Generex Biotechnology), GLP-1-derivatives such as, for example, exenatide, liraglutide or those which have been disclosed in WO 98/08871 or WO 2005/027978 of Novo Nordisk A/S, in WO 01/04156 of Zealand or in WO 00/34331 of Beaufour-Ipsen, Pramlintide Acetate (Symlin; Amylin Pharmaceuticals), and orally effective hypoglycemic active ingredients.

The active ingredients include preferably
sulfonylureas,
biguanidines,
meglitinides,
oxadiazolidinediones,
thiazolidinediones,
glucosidase inhibitors,
inhibitors of glycogen phosphorylase,
glucagon antagonists,
glucokinase activators,
inhibitors of fructose-1,6-bisphosphatase,
modulators of glucose transporter 4 (GLUT4),
inhibitors of glutamine-fructose-6-phosphate amidotransferase (GFAT), GLP-1 agonists,
potassium channel openers such as, for example, those which have been disclosed in
WO 97/26265 and WO 99/03861 of Novo Nordisk A/S,
inhibitors of dipeptidylpeptidase IV (DPP-IV),
insulin sensitizers,
inhibitors of liver enzymes involved in stimulating gluconeogenesis and/or glycogenolysis,
modulators of glucose uptake, of glucose transport and of glucose reabsorption, inhibitors of 11β-HSD1,
inhibitors of protein tyrosine phosphatase 1B (PTP1B),
modulators of the sodium-dependent glucose transporter 1 or 2 (SGLT1, SGLT2),
compounds which alter lipid metabolism such as antihyperlipidemic active ingredients and antilipidemic active ingredients,
compounds which reduce food intake,
compounds which increase thermogenesis,
PPAR and RXR modulators and
active ingredients which act on the ATP-dependent potassium channel of the beta cells.

In one embodiment of the invention, the compound of the formula I is administered in combination with an HMGCoA reductase inhibitor such as simvastatin, fluvastatin, pravastatin, lovastatin, atorvastatin, cerivastatin, rosuvastatin or L-659699.

In one embodiment of the invention, the compound of the formula I is administered in combination with a cholesterol absorption inhibitor such as, for example, ezetimibe, tiqueside, pamaqueside, FM-VP4 (sitostanol/campesterol ascorbyl phosphate; Forbes Medi-Tech, WO 2005/042692), MD-0727 (Microbia Inc., WO 2005/021497) or with compounds as described in WO 2002/066464 (Kotobuki Pharmaceutical Co. Ltd.), WO 2005/062824 (Merck & Co.) or WO 2005/061451 and WO 2005/061452 (AstraZeneca AB).

In one embodiment of the invention, the compound of the formula I is administered in combination with a PPAR gamma agonist such as, for example, rosiglitazone, pioglitazone, JTT-501, GI 262570, R-483 or CS-011 (rivoglitazone).

In one embodiment of the invention, the compound of the formula I is administered in combination with a PPAR alpha agonist such as, for example, GW9578, GW-590735, K-111, LY-674, KRP-101 or DRF-10945.

In one embodiment of the invention, the compound of the formula I is administered in combination with a mixed PPAR alpha/gamma agonist such as, for example, muraglitazar, tesaglitazar, naveglitazar, LY-510929, ONO-5129, E-3030 or as described in WO 00/64888, WO 00/64876, WO 03/020269, WO 2004/075891, WO 2004/076402, WO 2004/075815, WO 2004/076447, WO 2004/076428, WO 2004/076401, WO 2004/076426, WO 2004/076427, WO 2006/018118, WO 2006/018115, and WO 2006/018116 or in J. P. Berger et al., TRENDS in Pharmacological Sciences 28(5), 244-251, 2005.

In one embodiment of the invention, the compound of the formula I is administered in combination with a PPAR delta agonist such as, for example, GW-501516, or as described in WO 2005/097762, WO 2005/097786, WO2005/097763, WO 2006/029699.

In one embodiment of the invention, the compound of the formula I is administered in combination with metaglidasen or with MBX-2044 or other partial PPAR gamma agonists/antagonists.

In one embodiment of the invention, the compound of the formula I is administered in combination with a fibrate such as, for example, fenofibrate, clofibrate or bezafibrate.

In one embodiment of the invention, the compound of the formula I is administered in combination with an MTP inhibitor such as, for example, implitapide, BMS-201038, R-103757 or those described in WO 2005/085226.

In one embodiment of the invention, the compound of the formula I is administered in combination with a CETP inhibitor such as, for example, torcetrapib or JTT-705.

In one embodiment of the invention, the compound of the formula I is administered in combination with a bile acid absorption inhibitor (see, for example, U.S. Pat. Nos. 6,245,744, 6,221,897 or WO 00/61568), such as, for example, HMR 1741 or those as described in DE 10 2005 033099.1 and DE 10 2005 033100.9.

In one embodiment of the invention, the compound of the formula I is administered in combination with a polymeric bile acid adsorbent such as, for example, cholestyramine or colesevelam.

In one embodiment of the invention, the compound of the formula I is administered in combination with an LDL receptor inducer (see U.S. Pat. No. 6,342,512), such as, for example, HMR1171, HMR1586 or those as described in WO 2005/097738.

In one embodiment, the compound of the formula I is administered in combination with Omacor® (Omega-3 fatty acids; highly concentrated ethyl esters of eicosapentaenoic acid and of docosahexaenoic acid).

In one embodiment of the invention, the compound of the formula I is administered in combination with an ACAT inhibitor such as, for example, avasimibe.

In one embodiment of the invention, the compound of the formula I is administered in combination with an antioxidant such as, for example, OPC-14117, probucol, tocopherol, ascorbic acid, β-carotene or selenium.

In one embodiment of the invention, the compound of the formula I is administered in combination with a vitamin such as, for example, vitamin B6 or vitamin B12.

In one embodiment of the invention, the compound of the formula I is administered in combination with a lipoprotein lipase modulator such as, for example, ibrolipim (NO-1886).

In one embodiment of the invention, the compound of the formula I is administered in combination with an ATP citrate lyase inhibitor such as, for example, SB-204990.

In one embodiment of the invention, the compound of the formula I is administered in combination with a squalene synthetase inhibitor such as, for example, BMS-188494 or as described in WO 2005/077907.

In one embodiment of the invention, the compound of the formula I is administered in combination with a lipoprotein (a) antagonist such as, for example, gemcabene (CI-1027).

In one embodiment of the invention, the compound of the formula I is administered in combination with an HM74A receptor agonist such as, for example, nicotinic acid.

In one embodiment of the invention, the compound of the formula I is administered in combination with a lipase inhibitor such as, for example, orlistat or cetilistat (ATL-962).

In one embodiment of the invention, the compound of the formula I is administered in combination with insulin.

In one embodiment of the invention, the compound of the formula I is administered in combination with a sulfonylurea such as, for example, tolbutamide, glibenclamide, glipizide or glimepiride.

In one embodiment of the invention, the compound of the formula I is administered in combination with a biguanide such as, for example, metformin.

In another embodiment of the invention, the compound of the formula I is administered in combination with a meglitinide such as, for example, repaglinide or nateglinide.

In one embodiment of the invention, the compound of the formula I is administered in combination with a thiazolidinedione such as, for example, troglitazone, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinyl-methoxy]phenyl]methyl]-2,4-thiazolidinedione.

In one embodiment of the invention, the compound of the formula I is administered in combination with an α-glucosidase inhibitor such as, for example, miglitol or acarbose.

In one embodiment of the invention, the compound of the formula I is administered in combination with an active ingredient which acts on the ATP-dependent potassium channel of the beta cells, such as, for example, tolbutamide, glibenclamide, glipizide, glimepiride or repaglinide.

In one embodiment of the invention, the compound of the formula I is administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

In one embodiment of the invention, the compound of the formula I is administered in combination with an inhibitor of glycogen phosphorylase, such as, for example, PSN-357 or FR-258900 or those as described in WO 2003/084922, WO 2004/007455, WO 2005/073229-31 or WO 2005/067932.

In one embodiment of the invention, the compound of the formula I is administered in combination with glucagon receptor antagonists such as, for example, A-770077, NNC-25-2504 or as described in WO 2004/100875 or WO 2005/065680.

In one embodiment of the invention, the compound of the formula I is administered in combination with activators of glucokinase, such as, for example, RO-4389620, LY-2121260 (WO 2004/063179), PSN-105, PSN-110, GKA-50 or those as are described for example by Prosidion in WO 2004/072031, WO 2004/072066, WO 05/103021 or WO 06/016178, by Roche in WO 00/058293, WO 00/183465, WO 00/183478, WO 00/185706, WO 00/185707, WO 01/044216, GB 02385328, WO 02/008209, WO 02/014312, WO 02/46173, WO 02/48106, DE 10259786, WO 03/095438, US 04067939 or WO 04/052869, by Novo Nordisk in EP 1532980, WO 03/055482, WO 04/002481, WO 05/049019, WO 05/066145 or WO 05/123132, by Merck/Banyu in WO 03/080585, WO 03/097824, WO 04/081001, WO 05/063738 or WO 05/090332, by Eli Lilly in WO 04/063194, or by Astra Zeneca in WO 01/020327, WO 03/000262, WO 03/000267, WO 03/015774, WO 04/045614, WO 04/046139, WO 05/044801, WO 05/054200, WO 05/054233, WO 05/056530, WO 05/080359, WO 05/080360 or WO 05/121110.

In one embodiment of the invention, the compound of the formula I is administered in combination with an inhibitor of gluconeogenesis, such as, for example, FR-225654.

In one embodiment of the invention, the compound of the formula I is administered in combination with inhibitors of fructose-1,6-bisphosphatase (FBPase), such as, for example, CS-917.

In one embodiment of the invention, the compound of the formula I is administered in combination with modulators of glucose transporter 4 (GLUT4), such as, for example, KST-48 (D.-O. Lee et al.: Arzneim.-Forsch. Drug Res. 54 (12), 835 (2004)).

In one embodiment of the invention, the compound of the formula I is administered in combination with inhibitors of glutamine-fructose-6-phosphate amidotransferase (GFAT), as are described for example in WO 2004/101528.

In one embodiment of the invention, the compound of the formula I is administered in combination with inhibitors of dipeptidylpeptidase IV (DPP-IV), such as, for example, vildagliptin (LAF-237), sitagliptin (MK-0431), saxagliptin (BMS-477118), GSK-823093, PSN-9301, SYR-322, SYR-619, TA-6666, TS-021, GRC-8200, GW-825964x or as are described in WO 2003/074500, WO 2003/106456, WO 2004/

50658, WO 2005/058901, WO 2005/012312, WO 2005/012308, PCT/EP2005/007821, PCT/EP2005/008005, PCT/EP2005/008002, PCT/EP2005/008004, PCT/EP2005/008283, DE 10 2005 012874.2 or DE 10 2005 012873.4.

In one embodiment of the invention, the compound of the formula I is administered in combination with inhibitors of 11-beta-hydroxysteroid dehydrogenase 1 (11β-HSD1), such as, for example, BVT-2733 or those as are described for example in WO 2001/90090-94, WO 2003/43999, WO 2004/112782, WO 2003/44000, WO 2003/44009, WO 2004/112779, WO 2004/113310, WO 2004/103980, WO 2004/112784, WO 2003/065983, WO 2003/104207, WO 2003/104208, WO 2004/106294, WO 2004/011410, WO 2004/033427, WO 2004/041264, WO 2004/037251, WO 2004/056744, WO 2004/065351, WO 2004/089367, WO 2004/089380, WO 2004/089470-71, WO 2004/089896, WO 2005/016877 or WO 2005/097759.

In one embodiment of the invention, the compound of the formula I is administered in combination with inhibitors of protein tyrosine phosphatase 1B (PTP1B), as are described for example in WO 2001/19830-31, WO 2001/17516, WO 2004/506446, WO 2005/012295, PCT/EP2005/005311, PCT/EP2005/005321, PCT/EP2005/007151, PCT/EP2005/01294 or DE 10 2004 060542.4.

In one embodiment of the invention, the compound of the formula I is administered in combination with modulators of the sodium-dependent glucose transporter 1 or 2 (SGLT1, SGLT2), such as, for example, KGA-2727, T-1095 and SGL-0010 or as are described for example in WO 2004/007517, WO 2004/52903, WO 2004/52902, WO 2005/121161, WO 2005/085237, JP2004359630 or by A. L. Handlon in Expert Opin. Ther. Patents (2005) 15(11), 1531-1540.

In one embodiment of the invention, the compound of the formula I is administered in combination with inhibitors of hormone-sensitive lipase (HSL) as described for example in WO 01/17981, WO 01/66531, WO 2004/035550, WO 2005/073199 or WO 03/051842.

In one embodiment of the invention, the compound of the formula I is administered in combination with inhibitors of acetyl-CoA carboxylase (ACC), such as, for example, those as described in WO 1999/46262, WO 2003/72197, WO 2003/072197 or WO 2005/044814.

In one embodiment of the invention, the compound of the formula I is administered in combination with an inhibitor of phosphoenolpyruvate carboxykinase (PEPCK), such as, for example, those as described in WO 2004/074288.

In one embodiment of the invention, the compound of the formula I is administered in combination with an inhibitor of glycogen synthase kinase 3 beta (GSK-3 beta), as described for example in US2005222220, WO 2004/046117, WO 2005/085230, WO 2005/111018, WO 2003/078403, WO 2004/022544, WO 2003/106410, WO 2005/058908, US2005038023, WO 2005/009997, US2005026984, WO 2005/000836, WO 2004/106343, EP1460075, WO 2004/014910, WO 2003/076442, WO 2005/087727 or WO 2004/046117.

In one embodiment of the invention, the compound of the formula I is administered in combination with an inhibitor of protein kinase C beta (PKC beta), such as, for example, ruboxistaurin.

In one embodiment of the invention, the compound of the formula I is administered in combination with an endothelin A receptor antagonist such as, for example, avosentan (SPP-301).

In one embodiment of the invention, the compound of the formula I is administered in combination with inhibitors of "I-kappaB kinase" (IKK inhibitors), as are described for example in WO 2001/000610, WO 2001/030774, WO 2004/022553 or WO 2005/097129.

In one embodiment of the invention, the compound of the formula I is administered in combination with modulators of the glucocorticoid receptor, like those described for example in WO 2005/090336.

In a further embodiment of the invention, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558); NPY antagonists such as, for example, naphthalene-1-sulfonic acid {4-[(4-amino-quinazolin-2-ylamino)methyl]cyclohexylmethyl}amide hydrochloride (CGP 71683A); peptide YY 3-36 (PYY3-36) or analogous compounds, such as, for example, CJC-1682 (PYY3-36 conjugated with human serum albumin via Cys34), CJC-1643 (derivative of PYY3-36 which conjugates in vivo to serum albumin) or those as are described in WO 2005/080424;

cannabinoid receptor 1 antagonists such as, for example, rimonabant, SR147778 or those as are described for example in EP 0656354, WO 00/15609, WO 02/076949, WO 2005/080345, WO 2005/080328, WO 2005/080343, WO 2005/075450, WO 2005/080357, WO 2001/70700, WO 2003/026647-48, WO 2003/02776, WO 2003/040107, WO 2003/007887, WO 2003/027069, U.S. Pat. No. 6,509,367, WO 2001/32663, WO 2003/086288, WO 2003/087037, WO 2004/048317, WO 2004/058145, WO 2003/084930, WO 2003/084943, WO 2004/058744, WO 2004/013120, WO 2004/029204, WO 2004/035566, WO 2004/058249, WO 2004/058255, WO 2004/058727, WO 2004/069838, US20040214837, US20040214855, US20040214856, WO 2004/096209, WO 2004/096763, WO 2004/096794, WO 2005/000809, WO 2004/099157, US20040266845, WO 2004/110453, WO 2004/108728, WO 2004/000817, WO 2005/000820, US20050009870, WO 2005/00974, WO 2004/111033-34, WO 2004/11038-39, WO 2005/016286, WO 2005/007111, WO 2005/007628, US20050054679, WO 2005/027837, WO 2005/028456, WO 2005/063761-62, WO 2005/061509 or WO 2005/077897;

MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)) or LB53280, LB53279, LB53278 or THIQ, MB243, RY764, CHIR-785, PT-141 or those as are described in WO 2005/060985, WO 2005/009950, WO 2004/087159, WO 2004/078717, WO 2004/078716, WO 2004/024720, US20050124652, WO 2005/051391, WO 2004/112793, WOUS20050222014, US20050176728, US20050164914, US20050124636, US20050130988, US20040167201, WO 2004/005324, WO 2004/037797, WO 2005/042516, WO 2005/040109, WO 2005/030797, US20040224901, WO 2005/01921, WO 2005/09184, WO 2005/000339, EP1460069, WO 2005/047253, WO 2005/047251, EP1538159, WO 2004/072076, WO 2004/072077 or WO 2006/024390;

orexin receptor antagonists (e.g. 1-(2-methylbenzoxazol-6-yl)-3-[1,5]naphthyridin-4-ylurea hydrochloride (SB-334867-A) or those as are described for example in WO 2001/96302, WO 2001/85693, WO 2004/085403 or WO 2005/075458); histamine H3 receptor agonists (e.g. 3-cyclohexyl-1-(4,4-dimethyl-1,4,6,7-tetrahydro-imidazo[4, 5-c]pyridin-5-yl)propan-1-one oxalic acid salt (WO 00/63208) or those as are described in WO 2000/64884, WO 2005/082893);

CRF antagonists (e.g. [2-methyl-9-(2,4,6-trimethylphenyl)-9H-1,3,9-triazafluoroen-4-yl]dipropylamine (WO 00/66585));

CRF BP antagonists (e.g. urocortin); urocortin agonists;

β3 agonists (such as, for example, 1-(4-chloro-3-methane-sulfonylmethylphenyl)-2-[2-(2,3-dimethyl-1H-indol-6-yloxy)ethylamino]ethanol hydrochloride (WO 01/83451));

MSH (melanocyte-stimulating hormone) agonists;

MCH (melanin-concentrating hormone) receptor antagonists (such as, for example, NBI-845, A-761, A-665798, A-798, ATC-0175, T-226296, T-71, GW-803430 or compounds such as are described in WO 2003/15769, WO 2005/085200, WO 2005/019240, WO 2004/011438, WO 2004/012648, WO 2003/015769, WO 2004/072025, WO 2005/070898, WO 2005/070925, WO 2006/018280, WO 2006/018279, WO 2004/039780, WO 2003/033476, WO 2002/006245, WO 2002/002744, WO 2003/004027 or FR2868780);

CCK-A agonists (such as, for example, {2-[4-(4-chloro-2,5-dimethoxyphenyl)-5-(2-cyclohexylethyl)thiazol-2-ylcarbamoyl]-5,7-dimethylindol-1-yl}acetic acid trifluoroacetic acid salt (WO 99/15525), SR-146131 (WO 0244150) or SSR-125180);

serotonin reuptake inhibitors (e.g. dexfenfluramine);

mixed serotoninergic and noradrenergic compounds (e.g. WO 00/71549);

5-HT receptor agonists, e.g. 1-(3-ethylbenzofuran-7-yl)piperazine oxalic acid salt (WO 01/09111);

5-HT2C receptor agonists (such as, for example, APD-356, BVT-933 or those as are described in WO 2000/77010, WO 2007/7001-02, WO 2005/019180, WO 2003/064423, WO 2002/42304 or WO 2005/082859);

5-HT6 receptor antagonists as are described for example in WO 2005/058858;

bombesin receptor agonists (BRS-3 agonists);

galanin receptor antagonists;

growth hormone (e.g. human growth hormone or AOD-9604);

growth hormone releasing compounds (tertiary butyl 6-benzyloxy-1-(2-diisopropyl-aminoethylcarbamoyl)-3,4-dihydro-1H-isoquinoline-2-carboxylate (WO 01/85695));

growth hormone secretagogue receptor antagonists (ghrelin antagonists) such as, for example, A-778193 or those as are described in WO 2005/030734;

TRH agonists (see, for example, EP 0 462 884); uncoupling protein 2 or 3 modulators;

leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881);

DA agonists (bromocriptine or Doprexin);

lipase/amylase inhibitors (like those described for example in WO 00/40569);

inhibitors of diacylglycerol O-acyltransferases (DGATs) as described for example in US2004/0224997, WO 2004/094618, WO 2000/58491, WO 2005/044250, WO 2005/072740, JP2005206492 or WO 2005/013907;

inhibitors of fatty acid synthase (FAS) such as, for example, C75 or those as described in WO 2004/005277;

oxyntomodulin;

oleoyl-estrone or thyroid hormone receptor agonists such as, for example: KB-2115 or those as described in WO 2005/8279, WO 2001/72692, WO 2001/94293, WO 2003/084915, WO 2004/018421 or WO 2005/092316.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In one embodiment of the invention, the further active ingredient is dexamphetamine or amphetamine.

In one embodiment of the invention, the further active ingredient is fenfluramine or dexfenfluramine.

In another embodiment of the invention, the further active ingredient is sibutramine. In one embodiment of the invention, the further active ingredient is mazindole or phentermine.

In one embodiment of the invention, the compound of the formula I is administered in combination with bulking agents, preferably insoluble bulking agents (see, for example, Carob/Caromax® (Zunft H J; et al., Carob pulp preparation for treatment of hypercholesterolemia, ADVANCES IN THERAPY (2001 Sep.-Oct.), 18(5), 230-6)). Caromax is a carob-containing product from Nutrinova, Nutrition Specialties & Food Ingredients GmbH, Industriepark Hoechst, 65926 Frankfurt/Main. Combination with Caromax® is possible in one preparation or by separate administration of compounds of the formula I and Caromax®. Caromax® can in this connection also be administered in the form of food products such as, for example, in bakery products or muesli bars.

In one embodiment of the invention, the compound of the formula I is administered in combination with PDE inhibitors (phosphodiesterase), like those described for example in WO 2003/077949 or WO 2005/012485.

In one embodiment of the invention, the compound of the formula I is administered in combination with NAR-1 (nicotinic acid receptor) agonists like those described for example in WO 2004/094429.

In one embodiment of the invention, the compound of the formula I is administered in combination with CB2 (cannabinoid receptor) agonists like those described for example in US2005/143448.

In one embodiment of the invention, the compound of the formula I is administered in combination with histamine 1 agonists like those described for example in WO 2005/101979.

In one embodiment of the invention, the compound of the formula I is administered in combination with bupropion as described in WO 2006/017504.

In one embodiment of the invention, the compound of the formula I is administered in combination with opioid antagonists like those described for example in WO 2005/107806 or WO 2004/094429.

In one embodiment of the invention, the compound of the formula I is administered in combination with neutral endopeptidase inhibitors like those described for example in WO 2002/02513, WO 2002/06492, WO 2002/040008, WO 2002/040022 or WO 2002/047670.

In one embodiment of the invention, the compound of the formula I is administered in combination with NPY inhibitors (neuropeptide Y) like those described for example in WO 2002/047670.

In one embodiment of the invention, the compound of the formula I is administered in combination with sodium/hydrogen exchange inhibitors like those described for example in WO 2003/092694.

In one embodiment of the invention, the compound of the formula I is administered in combination with modulators of the glucocorticoid receptor like those described for example in WO 2005/090336.

In one embodiment of the invention, the compound of the formula I is administered in combination with nicotine receptor agonists like those described for example in WO 2004/094429.

In one embodiment of the invention, the compound of the formula I is administered in combination with NRIs (norepinephrine reuptake inhibitors) like those described for example in WO 2002/053140.

In one embodiment of the invention, the compound of the formula I is administered in combination with MOA (E-beta-methoxyacrylate) such as, for example, segeline or like those described for example in WO 2002/053140.

In one embodiment of the invention, the compound of the formula I is administered in combination with antithrombotic active ingredients such as, for example, clopidogrel.

It will be appreciated that every suitable combination of the compounds of the invention with one or more of the aforementioned compounds and optionally one or more other pharmacologically active substances is regarded as falling within the protection conferred by the present invention.

Some of the formulae for the development codes mentioned above are detailed hereinafter.

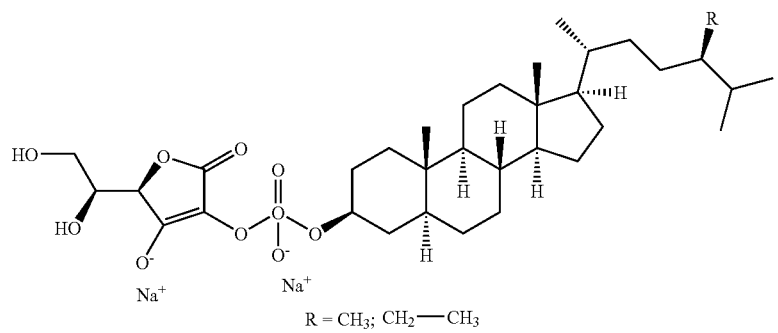

R = CH₃; CH₂—CH₃

FM-VP4

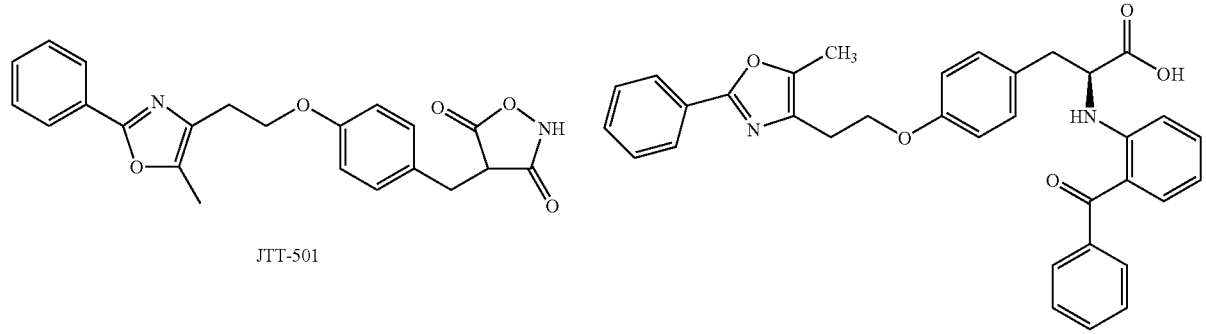

JTT-501

GI 262570

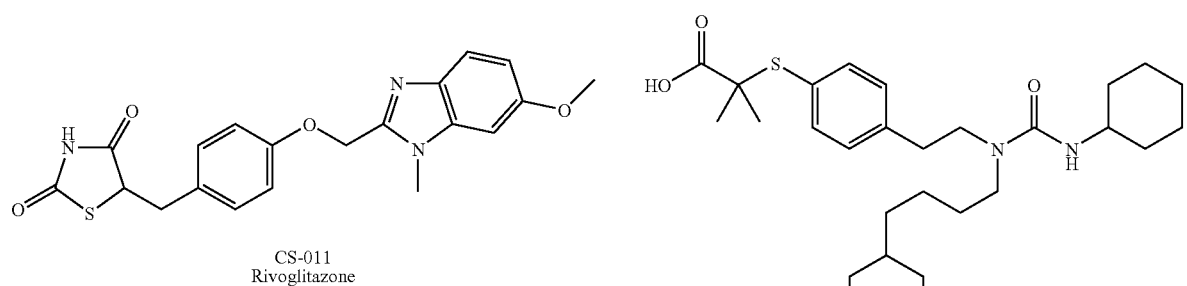

CS-011
Rivoglitazone

GW-9578

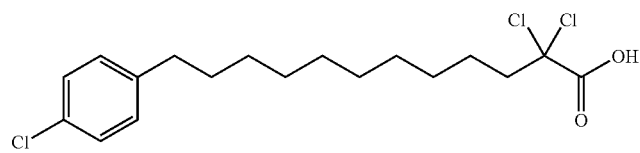

K-111

-continued
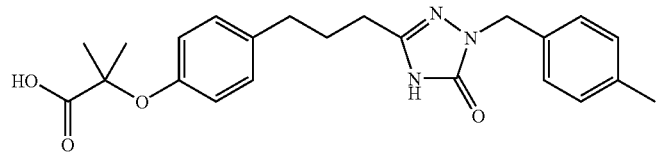
LY-674
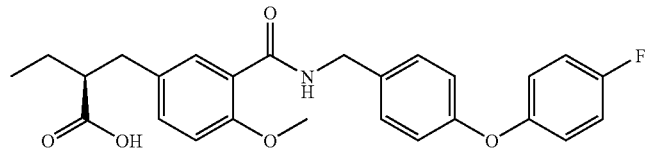
KRP-101
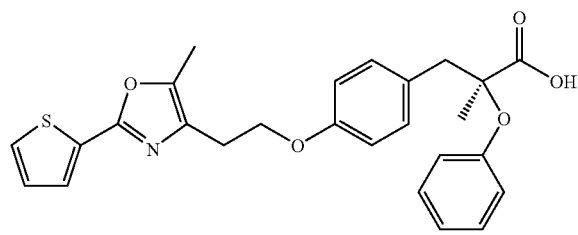
LY-510929
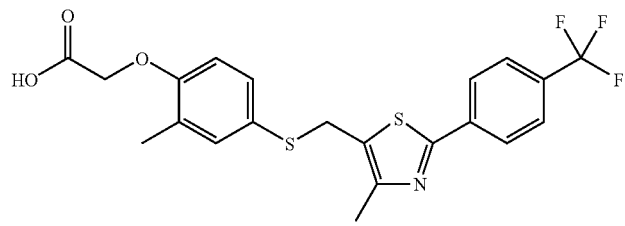
GW-501516
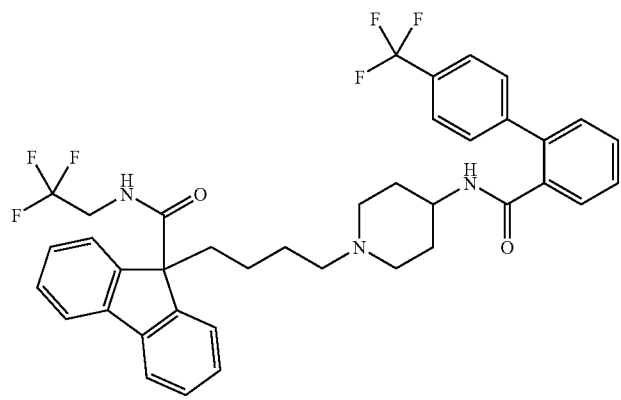
BMS-201038

-continued
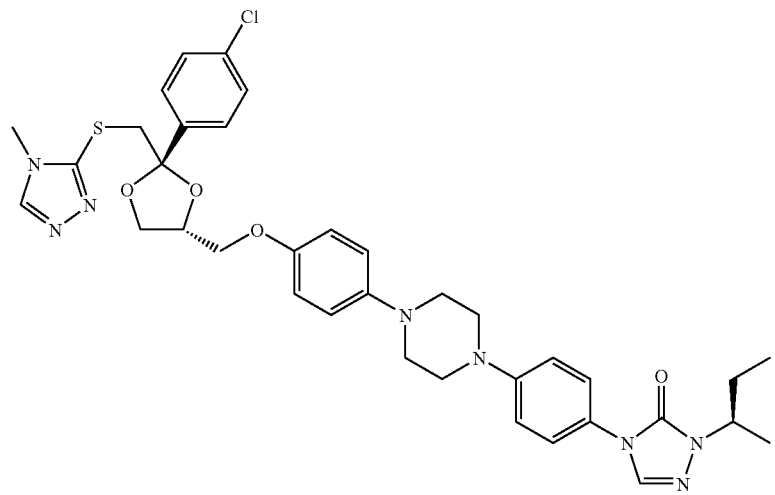
R-103757
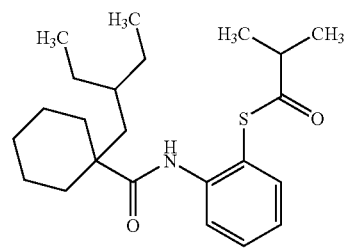
JTT-705
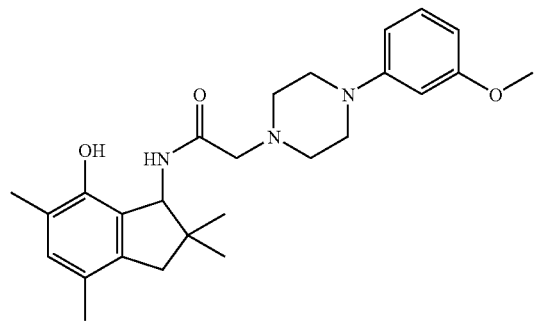
OPC-14117
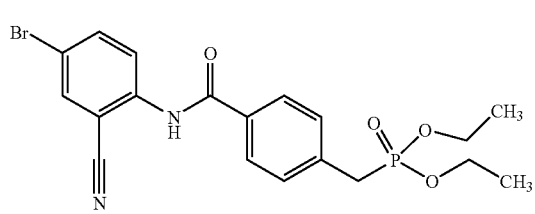
NO-1886
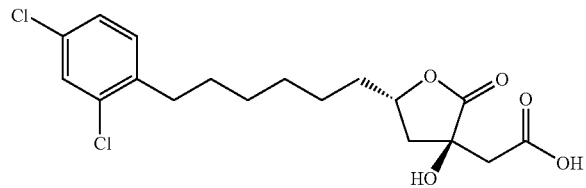
SB-204990
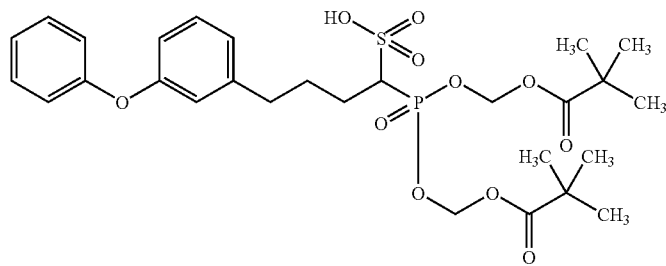
BMS-188494

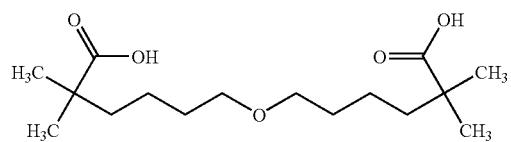
CI-1027
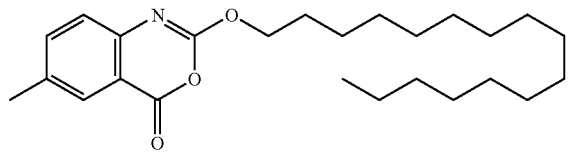
ATL-962
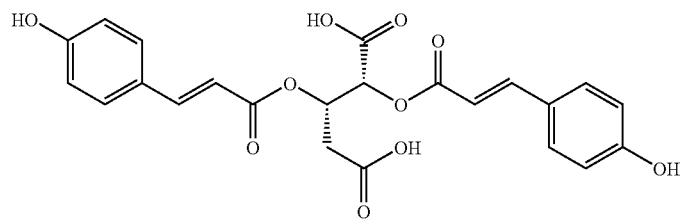
FR-258900
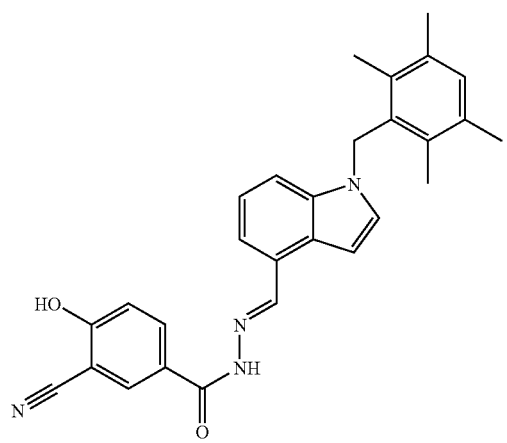
NNC-25-2504
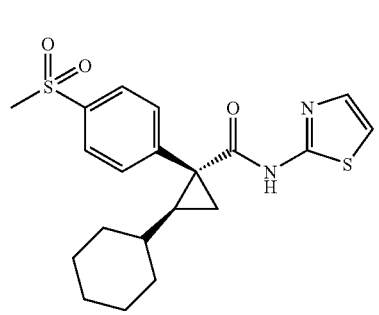
LY-2121260
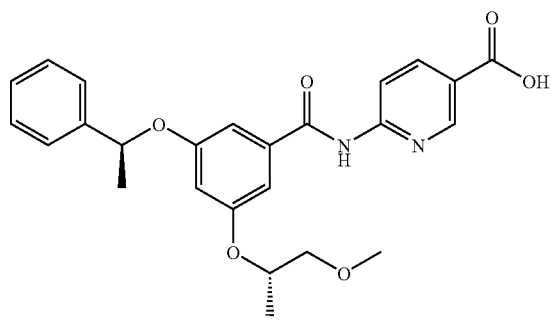
GKA-50

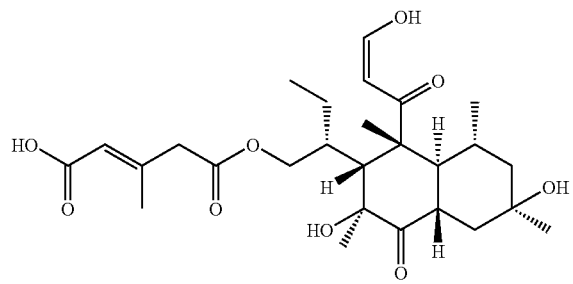
FR-225654
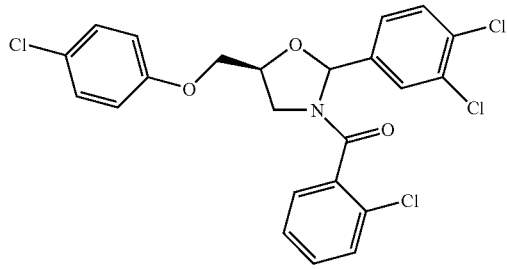
KST-48
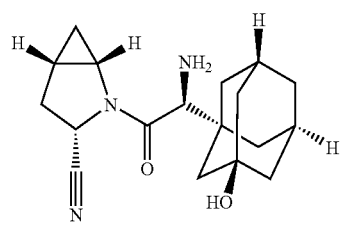
BMS-477118
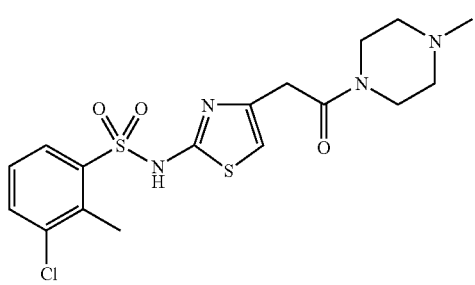
BVT-2733
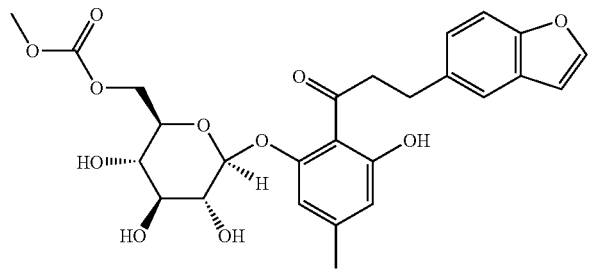
T-1095
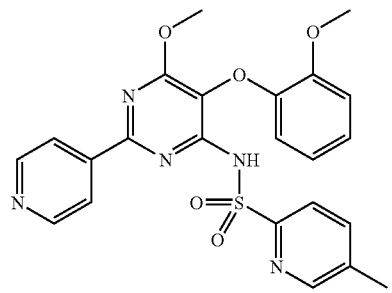
SPP-301
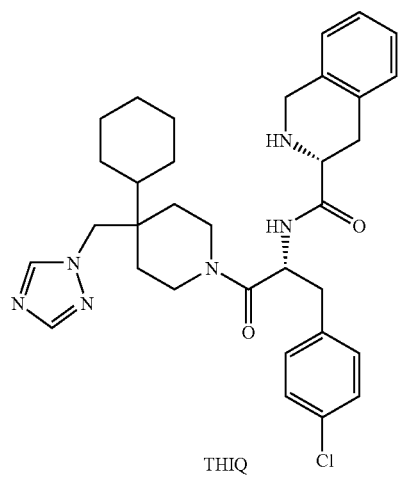
THIQ
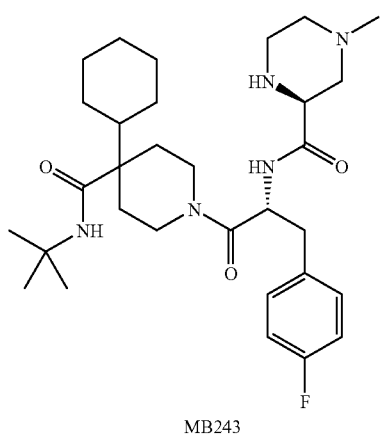
MB243

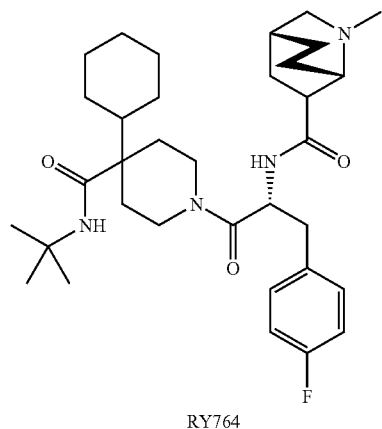
RY764
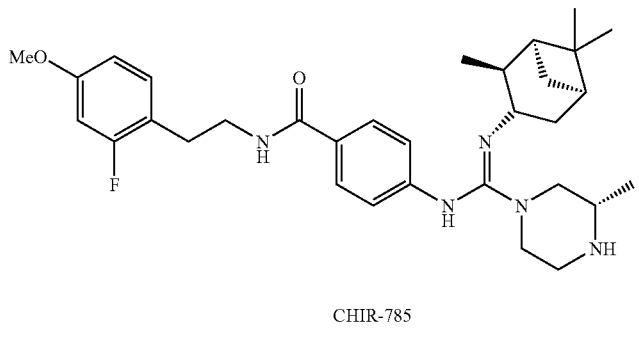
CHIR-785
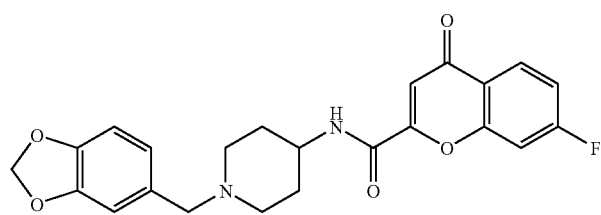
A-761
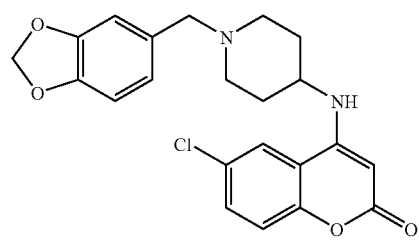
A-665798
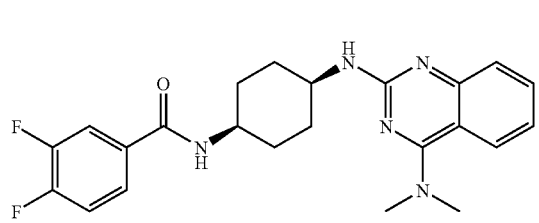
ATC-0175
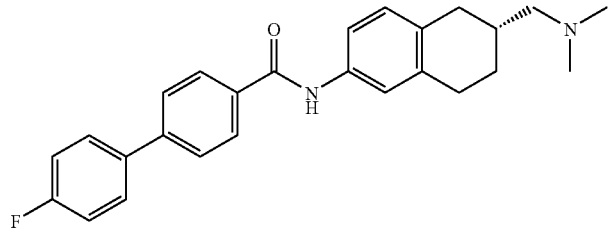
T-226296
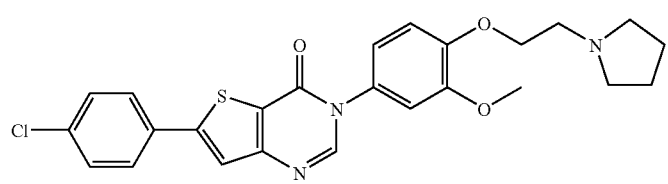 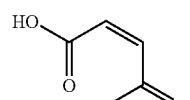
GW-803430

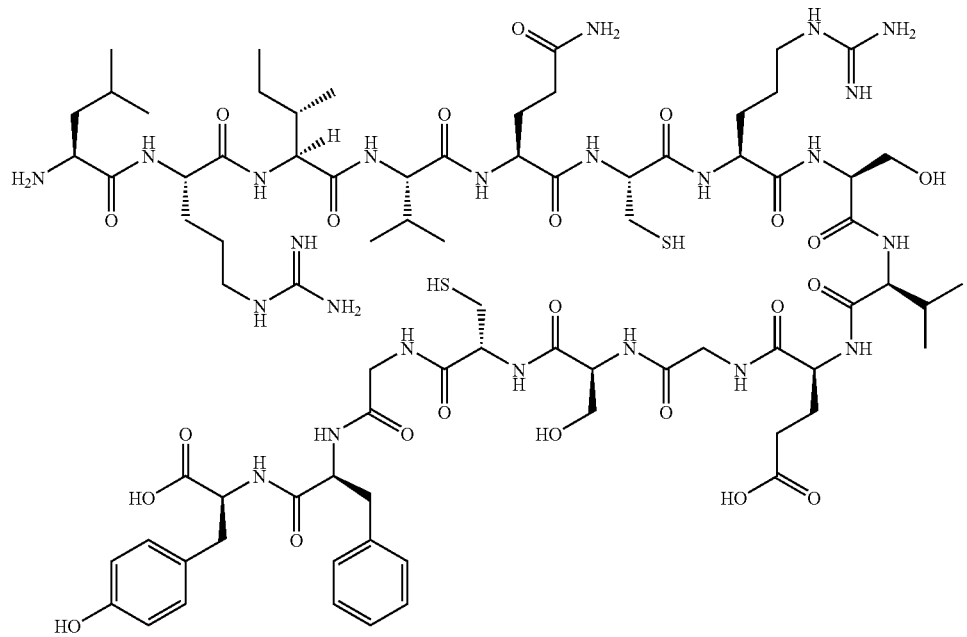
AOD-9604
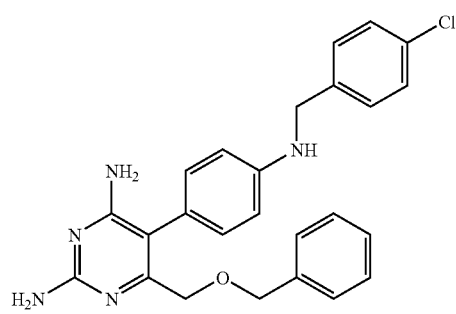
A-778193
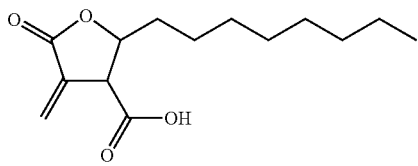
C75
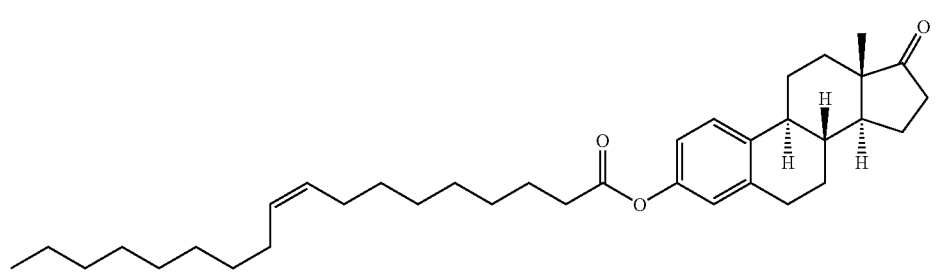
oleoyl-estrone
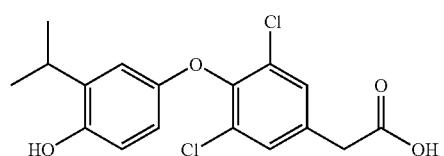
KB-2115

The activity of the compounds of the invention of the formula I was tested in the following enzyme assay system:

EL Inhibition Assay:

EL is released as secretory protein in high concentration into cell culture medium (conditioned medium) by recombinant cell lines (CHO, HEK293). This is employed as an enzyme solution after concentration.

EL Activity Assay

The phospholipase-specific substrate 1,2-bis(4,4-difluoro-5,7-dimethyl-4-bora-3a,4a-diaza-s-indacene-3-undecanoyl)-sn-glycero-3-phosphocholine (manufacturer Molecular Probes) is used to characterize the enzymatic activity of endothelial lipase and the effect of inhibitors. Hydrolysis of the A1 ester linkage of this phospholipid by the enzyme liberates a fatty acid labeled with the fluorescent dye Bodipy which can be detected after separation by thin-layer chromatography on an HPTLC plate (silica gel 60, Merck) or directly in the reaction vessel by measuring the fluorescence. The substrate solution is prepared by dissolving 100 µg of 1,2-bis(4,4-difluoro-5,7-dimethyl-4-bora-3a,4a-diaza-s-indacene-3-undecanoyl)-sn-glycero-3-phospho-choline (manufacturer Molecular Probes) in 100 µl of DMSO and taking up in 2.4 mg of tripalmitin (Sigma) in 393 µl of chloroform which comprises 20 mg/ml of DOP-choline (1,2-dioleoyl-sn-glycero-3-phosphocholine). 39.3 µl of this lipid mixture are transferred into a fresh reaction vessel, and the solvent is evaporated off. The lipid mixture is dissolved in 4 ml of 200 mM TRIS-HCl, 150 mM sodium chloride, pH=7.4, by sonicating twice. The subsequent enzymic reaction takes place at 37° C. for 90 minutes. For this purpose, 20 µl of the substrate solution are incubated with 2 µl of inhibitor of appropriate concentration (dissolved in 10% DMSO, using 10% strength DMSO solution for control) and 2 µl of enzyme solution (conditioned medium). Subsequently, 4 µl of the assay mixture are loaded onto an HPTLC plate (silica gel 60, Merck), and the liberated fluorescent dye is separated for detection with a mobile phase (diethyl ether:petroleum spirit: acetic acid [78:22:1]). After evaporation of the mobile phase, the plate is read in a fluorescence scanner. An increased liberation of the fluorescent dye in the uninhibited reaction is observed as a measure of the enzyme activity.

The enzymatic activity is reduced as a function of the inhibitor concentration used, and the inhibitor concentration at which a half-maximum enzymatic activity is observed is called $IC_{50}$.

In these assays, the compounds of the examples exhibited the following $IC_{50}$ values:

| Example | $IC_{50}$ [µM] EL |
| --- | --- |
| 1 | 0.06 |
| 2 | 0.24 |
| 7 | 0.146 |
| 8 | 0.226 |
| 9 | 0.232 |

Other Test Models

Suitability of the compounds of the invention as active pharmaceutical ingredient can be tested by means of various test models. Descriptions are given of such test models by way of example below.

Solubility in Aqueous Systems

Adequate solubility of a substance in aqueous solvent systems is an important prerequisite for a (reproducible) pharmacological effect. Solubilities in aqueous systems can be determined by various methods. Suitable examples of solution precipitation methods ("kinetic solubility") and methods which investigate the dissolution of a solid sample until an equilibrium is set up ("thermodynamic solubility").

a) Kinetic Solubility

A DMSO solution of the test compound (2.5 mM; 0.5 µL) is pipetted into 200 µL of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 µM using a nephelometer (e.g. Nephelostar Galaxy, BMG Labtech). The concentration of the test compound in the aqueous test solution is then raised to a theoretical 12.5 µM by adding further DMSO solution (2.5 mM; 0.5 µL), and the turbidity measurement is repeated. Further additions of DMSO solutions (1 µL, 2.5 mM; 0.5 µL, 10 mM; then 9× 1 µL, 10 mM resulting in theoretical concentrations of 25 µM, 50 µM, 100 µM, 150 µM, 200 µM, 250 µM, 300 µM, 350 µM, 400 µM, 450 µM and 500 µM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values <6.25 µM, 6.25-500 µM and >500 µM.

Preferred compounds of the invention show a kinetic solubility in phosphate buffer (pH 7.4) of at least 12.5 µM; more preferably of at least 50 µM and even more preferably of at least 250 µM.

b) Thermodynamic Solubility

The integrated UV absorption from HPLC UV measurement of serial dilutions of the test compound in DMSO (500 µM, 100 µM, 50 µM, 10 µM and 1 µM) shows a linear correlation with the concentration in a calibration line. The test compound (500 µg) is shaken together with the aqueous test solution (250 µL) in a closed vessel (capacity: 1.5 mL) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration lines and stated as solubility of the test compound in the respective aqueous test solution.

Examples of aqueous test solutions are deionized water or aqueous phosphate buffer with various pH values (e.g. pH 1.2; pH 4.0; pH 6.8; pH 7.4; pH 9.0) which can be prepared from the commercial solution (phosphate buffered saline, 10x, Sigma) by dilution and adjustment with phosphoric acid or sodium hydroxide solution by standard methods.

Preferred compounds of the invention show a solubility in phosphate buffer (pH 7.4) of at least 12.5 µM; more preferably of at least 50 µM and even more preferably of at least 250 µM.

Metabolic Stability

The metabolic stability is determined by incubating the test compound (5 μM) with microsomal liver fractions (1 mg/mL protein with 0.1% w/v BSA; 1 mM NADPH, 0.5% DMSO) at 37° C. Analysis at an incubation time of 0 and 20 minutes takes place by means of LCMS/MS. Further descriptions of the test system and references for the experimental procedure are to be found in Plant, N.; Drug Discovery Today 2004, 9(7), 328-336 and Lau, Y. Y. et al.; Pharmaceutical Res. 2002, 19(11), 1606-1610.

Process for Preparation

The inventive compounds of the formula I are prepared by methods known per se, for example by acylating substituted or unsubstituted imidazopyridin-2-one derivatives II with carbamoyl chlorides III (method A) or in two stages by reacting imidazopyridin-2-one derivatives II with phosgene or equivalents, such as trichloromethyl chlorocarbonate, di(trichloromethyl) carbonate or 4-nitrophenyl chloroformate, and further reacting the resulting imidazopyridin-2-one carboxylic acid derivatives with amines IV (method B). It is likewise also possible to react the imidazopyridin-2-one derivatives II with the corresponding isocyanates V R1–N=C=O (method C).

The R6 radicals may also be introduced subsequently by alkylating the compounds I (where R6=hydrogen) by literature methods.

R6 radicals of the —(C=O)—NR1'R2 type can be introduced by the above-mentioned methods A, B or C. This can be done by using components IV and phosgene, or III or V in a more than 2-fold excess relative to the starting compounds II.

The R6 radicals may also be introduced subsequently by the abovementioned methods A, B or C, especially when R1 and R1' are different.

R6 radicals of the —(C=O)—O—R1" type can be introduced by literature methods, either by reaction of unsubstituted imidazopyridin-2-ones with the corresponding chloroformates in order to arrive at the compounds of the formula II, which are reacted further as described above for A, B or C, or by subsequently reacting of compounds of the formula I where R6=H with the corresponding chloroformates.

The compounds of the formula I obtained by above-described processes can be separated by known separation processes, for example chromatographic processes, in order to isolate, for example, monosubstituted from disubstituted imidazopyridin-2-ones.

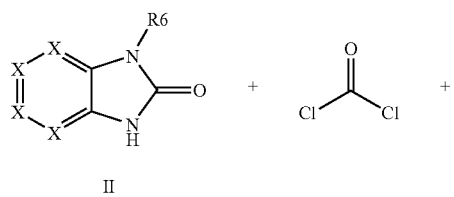

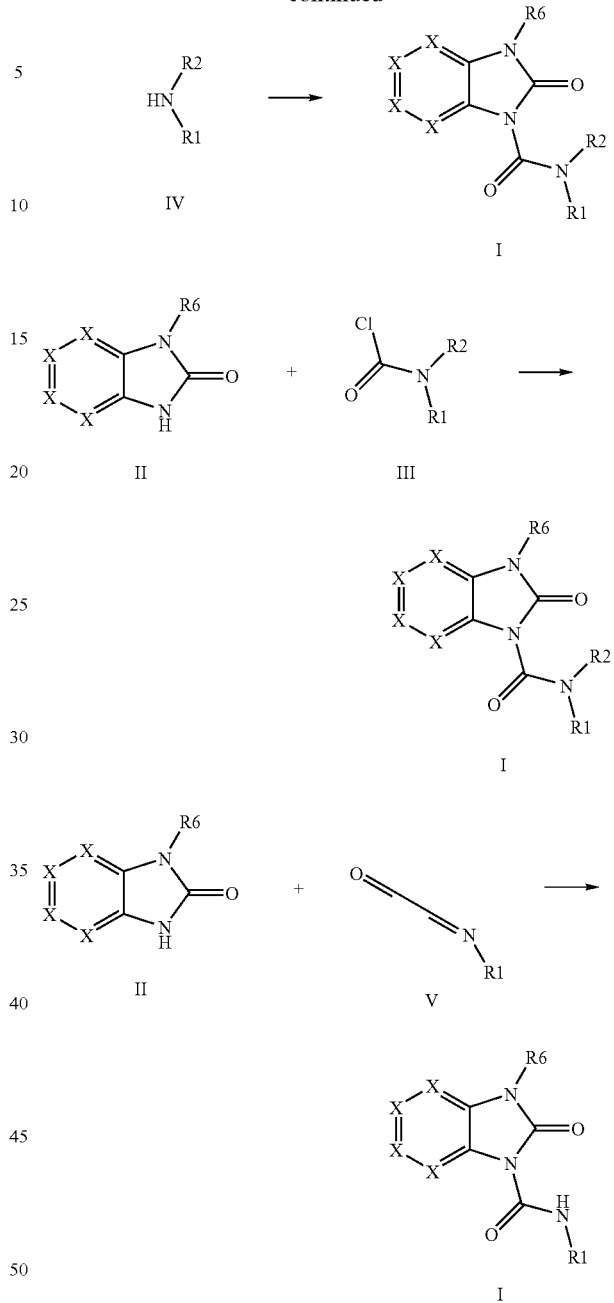

Since acids are generally released in these reactions, it is advisable to add bases such as pyridine, triethylamine, sodium hydroxide solution or alkali metal carbonates for acceleration. The reactions may be performed within wide temperature ranges. In general, it has been found to be advantageous to work at from 0° C. up to the boiling point of the solvent used. The solvents used include, for example, methylene chloride, THF, DMF, toluene, ethyl acetate, n-heptane, dioxane, diethyl ether or pyridine. When anhydrous conditions are employed, strong bases such as lithium hydride, sodium hydride or potassium tert-butoxide in aprotic solvents such as THF or DMF have also been found to be useful.

The imidazopyridin-2-one derivatives used are starting compounds II are commercially available or can be prepared by literature processes (for example, G. P. Zecchini, I. Torrini and M. P. Paradisi, J. Het. Chem. (1985) 22, 313-318; G. P. Zecchini, I. Torrini and M. P. Paradisi, J. Het. Chem. (1985) 22, 1061-1064).

The examples adduced below serve to illustrate the invention but without restricting it.

The identity of the compounds was checked by mass spectrometry.

EXAMPLES

Example 1

N-Hexyl-1-methyl-2-oxo-1,2-dihydroimidazo[4,5-b]pyridine-3-carboxamide

1-Methyl-1,3-dihydroimidazo[4,5-b]pyridin-2-one (75 mg, 0.5 mmol) and 1-isocyanatohexane (64 mg, 0.5 mmol) were stirred at 80° C. in 3.5 ml of dioxane for 4 h. The reaction mixture was concentrated and purified by means of preparative HPLC (PR18, acetonitrile/water 0.1% TFA). Yield: 40 mg (29%), M+H+: 277.16.

Example 2

N-(2-Methylbenzyl)-1-methyl-2-oxo-1,2-dihydroimidazo[4,5-b]pyridine-3-carboxamide Analogously to Example 1, 75 mg (0.5 mmol) of 1-methyl-1,3-dihydroimidazo[4,5-b]pyridin-2-one were reacted with 74 mg (0.5 mmol) of 1-isocyanatomethyl-2-methylbenzene in dioxane at 80° C. Yield: 11 mg (7%), M+H+: 297.05.

Example 3

N-Hexyl-2-oxo-2,3-dihydroimidazo[4,5-b]pyridine-1-carboxamide

Analogously to Example 1,1,3-dihydroimidazo[4,5-b]pyridin-2-one (100 mg, 0.74 mmol) and 1-isocyanatohexane (113 mg, 0.89 mmol) were reacted in dioxane. Yield: 75 mg (39%), M+H+: 263.15.

Example 4

N-Hexyl-3-methyl-2-oxo-2,3-dihydroimidazo[4,5-b]pyridine-1-carboxamide

In 2.5 ml of DMF, N-hexyl-2-oxo-2,3-dihydroimidazo[4,5-b]pyridine-1-carboxamide (65 mg, 0.248 mmol), iodomethane (70 mg, 0.5 mmol) and cesium carbonate (80 mg, 0.25 mmol) were stirred at RT for 5 h. After concentration, the mixture was admixed with water and ethyl acetate, and the organic phase was removed, concentrated and purified by means of preparative HPLC (PR18, acetonitrile/water 0.1% TFA). Yield: 16 mg (23%), M+H+: 277.17.

Example 5

N-Hexyl-7-methyl-2-oxo-1,2-dihydroimidazo[4,5-b]pyridine-3-carboxamide

Analogously to Example 1, tert-butyl 7-methyl-2-oxo-2,3-dihydroimidazo[4,5-b]pyridine-1-carboxylate (300 mg, 1.2 mmol), 1-isocyanatohexane (183.8 mg, 1.44 mmol) and 4-dimethylaminopyridine (14.7 mg, 0.12 mmol) were reacted in toluene. Yield: 8 mg (2%), M+H+: 277.16.

Example 6

N-Hexyl-7-methyl-2-oxo-1,2-dihydroimidazo[4,5-c]pyridine-3-carboxamide

Analogously to Example 1, 2 g (14.8 mmol) of 1,3-dihydroimidazo[4,5-c]pyridin-2-one and 1-isocyanatohexane (2.26 g, 17.76 mmol) were reacted in toluene. Yield: 43 mg (1%), M+H+: 263.19.

Example 7 tert-Butyl 3-hexylcarbamoyl-7-methyl-2-oxo-2,3-dihydroimidazo[4,5-b]pyridine-1-carboxylate Analogously to Example 1, tert-butyl 7-methyl-2-oxo-2,3-dihydroimidazo[4,5-b]pyridine-1-carboxylate (200 mg, 0.8 mmol) and 1-isocyanatohexane (113 mg, 0.88 mmol) were reacted in dioxane. Yield: 5 mg (2%), M+H+: 377.20.

Example 8

N,N'-Bishexyl-2-oxoimidazo[4,5-c]pyridine-1,3-dicarboxamide

As a further compound, N,N'-bishexyl-2-oxoimidazo[4,5-c]pyridine-1,3-dicarboxamide was isolated from the mixture in Example 6. Yield: 16 mg (1%), M+H+: 390.28.

Example 9

1-Methyl-2-oxo-1,2-dihydro-imidazo[4,5-b]pyridine-3-carboxylic acid-(R)-indan-1-ylamide As a further example 1-Methyl-2-oxo-1,2-dihydro-imidazo[4,5-b]pyridine-3-carboxylic acid-(R)-indan-1-ylamide was prepared analogously: M+H+: 309.21.

We claim:

1. A compound of formula (I)

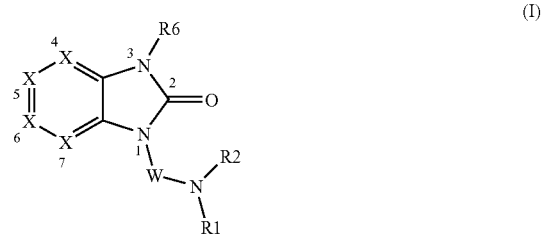

wherein:
X is =N— at one of the 4,5,6 and 7-positions, and is =C(—R)— at the other positions;
W is —(C=O)—[[, —(S=O)—, or —(SO$_2$)—]];
R is the same or different and is hydrogen, halogen, (C$_1$-C$_6$)-alkyl, (C$_1$-C$_3$)-haloalkyl, (C$_1$-C$_3$)-alkoxy-(C$_1$-C$_3$)-alkylene, aryl, heterocyclyl, hydroxyl, (C$_1$-C$_6$)-alkoxy, (C$_1$-C$_3$)-haloalkoxy, aryloxy, cyano, nitro, —S(O)$_p$—(C$_1$-C$_6$)-alkyl, where p=0, 1 or 2, aminosulfonyl, pentafluorosulfanyl, amino, (C$_1$-C$_6$)-alkylamino, di-(C$_2$-C$_{12}$)-alkylamino, (C$_1$-C$_6$)-alkylcarbonyl, COOR3, CO—NR4R5,O—CO—NR4R5, O—CO—(C$_1$-C$_6$)-alkylene-CO—O—(C$_1$-C$_6$)-alkyl, O—CO—(C$_1$-C$_6$)-alkylene-CO—OH, or O—CO—(C$_1$-C$_6$)-alkylene-CO—NR4R5;
R1 is (C$_5$-C$_{16}$)-alkyl, (C$_1$-C$_4$)-alkylenearyl, or indanyl, wherein the aryl, indanyl moiety is optionally mono- or polysubstituted by halogen, $(C_1-C_6)$-alkyl, $(C_1-C_6)$-alkoxy, hydroxyl, $(C_1-C_6)$-alkylmercapto, amino, $(C_1-C_6)$-alkylamino, di-$(C_2-C_{12})$-alkylamino, mono-$(C_1-C_6)$-alkylaminocarbonyl, di-$(C_2-C_8)$-alkylaminocarbonyl, $(C_1-C_6)$-alkyloxycarbonyl, $(C_1-C_6)$-alkylcarbonyl, cyano, nitro, trifluoromethyl, trifluoromethyloxy, pentafluorosulfanyl, $(C_1-C_6)$-alkylsulfonyl, or aminosulfonyl;

R1' is $(C_5-C_{16})$-alkyl;
R1" is $(C_1-C_{16})$-alkyl,
R2 is hydrogen;
R3 is hydrogen, $(C_1-C_6)$-alkyl, or benzyl;
R4 and R5 are each independently hydrogen, $(C_1-C_6)$-alkyl, aryl, $(C_3-C_{12})$-cycloalkyl, $(C_1-C_4)$-alkylenearyl, or $(C_1-C_3)$-alkylene-$(C_3-C_{12})$-cycloalkyl; and
R6 is hydrogen, $(C_1-C_{10})$-alkyl,
—(C=O)—NR1'R2, or
—(C=O)—O—R1";
or a tautomeric form thereof, or a physiologically compatible salt thereof.

2. The compound according to claim 1, wherein
R is the same or different and is hydrogen, halogen, $(C_1-C_6)$-alkyl, hydroxyl, phenoxy, trifluoromethyl, COOR3, pentafluorosulfanyl, amino, $(C_1-C_6)$-alkylamino, di-$(C_2-C_8)$-alkylamino, $(C_1-C_6)$-alkylsulfonyl, aminosulfonyl, phenyl, (C5-C7)-heterocycle, $(C_1-C_6)$-alkylcarbonyl, CO—NR4R5, O—CO—NR4R5, O—CO—$(C_1-C_6)$-alkylene-CO—O—$(C_1-C_6)$-alkyl, O—CO—$(C_1-C_6)$-alkylene-CO—NR4R5 or unsubstituted or mono- or poly-F-substituted $(C_1-C_3)$-alkyloxy;
R1 is $(C_6-C_{12})$-alkyl, $(C_1-C_3)$-alkylenearyl, or indanyl, wherein the aryl, or indanyl moiety is optionally mono- or polysubstituted by halogen, $(C_1-C_6)$-alkyl, $(C_1-C_3)$-alkyloxy, hydroxyl, amino, $(C_1-C_6)$-alkylamino, $(C_1-C_6)$-alkyloxycarbonyl, $(C_1-C_6)$-alkylcarbonyl, cyano, trifluoromethyl, or trifluoromethyloxy;
R1' is $(C_6-C_{12})$-alkyl;
R1" is $(C_1-C_{12})$-alkyl; and
R4 and R5 are each independently hydrogen, $(C_1-C_6)$-alkyl, $(C_3-C_{12})$-cycloalkyl, phenyl, $(C_1-C_4)$-alkylenephenyl, or $(C_1-C_4)$-alkylene-$(C_4-C_{12})$-cycloalkyl;
or a tautomeric form thereof, or a physiologically compatible salt thereof.

3. The compound according to claim 1, wherein
X in positions 4, 5 and 6 are identical or different and are each =C(—R)—, and in position 7 is =N—;
or a tautomeric form thereof, or a physiologically compatible salt thereof.

4. The compound according to claim 1, wherein
R is the same or different and is hydrogen, halogen, $(C_1-C_6)$-alkyl, trifluoromethyl, hydroxyl, amino, $(C_1-C_6)$-alkylcarbonyl, COOR3, $(C_1-C_6)$-alkylsulfonyl, pentafluorosulfanyl, or unsubstituted or mono- or poly-F-substituted $(C_1-C_3)$-alkyloxy;
R1 is $(C_6-C_{10})$-alkyl, —CH$_2$-phenyl, or, and the phenyl or indanyl moiety is optionally mono- to disubstituted by halogen, $(C_1-C_6)$-alkyl, $(C_{1-C_6})$-alkyloxy, hydroxyl, amino, $(C_1-C_6)$-alkoxycarbonyl, $(C_1-C_6)$-alkylcarbonyl, cyano, trifluoromethyl, or trifluoromethyloxy;
R1' is $(C_6-C_{10})$-alkyl;
R1" is $(C_1-C_{10})$-alkyl;
R3 is hydrogen, or $(C_1-C_6)$-alkyl; and
R6 is hydrogen, $(C_1-C_8)$-alkyl,
—(C=O)—NR1'R2, or
—(C=O)—O—R1";
or a tautomeric form thereof, or a physiologically compatible salt thereof.

5. The compound according to claim 1, wherein
R is the same or different and is hydrogen, halogen, hydroxyl, $(C_1-C_6)$-alkyloxy, trifluoromethyl, $(C_1-C_6)$-alkylcarbonyl or $(C_1-C_6)$-alkyl;
R1 is $(C_6-C_{10})$-alkyl, —CH$_2$-phenyl or indanyl, and the phenyl or indanyl is optionally mono- to disubstituted by halogen, $(C_1-C_6)$-alkyl, $(C_1-C_3)$-alkyloxy, $(C_1-C_6)$-alkylcarbonyl, or trifluoromethyl;
R1' is $(C_6-C_{10})$-alkyl;
R1" is $(C_1-C_{10})$-alkyl; and
R6 is hydrogen, $(C_1-C_4)$-alkyl,
—(C=O)—NR1'R2, or
—(C=O)—O—R1";
or a tautomeric form thereof, or a physiologically compatible salt thereof.

6. The compound according to claim 1, wherein
R is the same or different and is hydrogen, or methyl;
R1 is $(C_6-C_{10})$-alkyl, —CH$_2$-phenyl or bicycle of formula Id

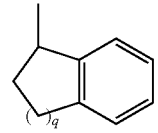

wherein q is 1, and the phenyl or bicycle moiety of formula Id is optionally substituted by methyl;
R1' is $(C_6-C_{10})$-alkyl; and
R6 is hydrogen, methyl, or —(C=O)—NR1'R2;
or a tautomeric form thereof, or a physiologically compatible salt thereof.

7. A pharmaceutical composition comprising the compound according to claim 1, or a tautomeric form thereof, or a physiologically compatible salt thereof, and a pharmaceutically acceptable carrier.

8. The pharmaceutical composition according to claim 7, further comprising at least one additional active ingredient selected from the group consisting of antidiabetics, active hypoglycemic ingredients, HMG-CoA reductase inhibitors, cholesterol absorption inhibitors, PPAR gamma agonists, PPAR alpha agonists, PPAR alpha/gamma agonists, fibrates, MTP inhibitors, bile acid absorption inhibitors, CETP inhibitors, polymeric bile acid adsorbents, LDL receptor inducers, ACAT inhibitors, antioxidants, lipoprotein lipase inhibitors, ATP citrate lyase inhibitors, squalene synthetase inhibitors, lipoprotein(a) antagonists, lipase inhibitors, insulins, sulfonylureas, biguanides, meglitinides, thiazolidinediones, α-glucosidase inhibitors, active ingredients which act on the ATP-dependent potassium channel of the beta cells, CART agonists, NPY agonists, MC4 agonists, orexin antagonists, H3 agonists, TNF agonists, CRF antagonists, CRF BP antagonists, urocortin agonists, β3 agonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists, bromocriptine, doprexin, lipase inhibitors, amylase inhibitors, PPAR modulators, RXR modulators, TR-β agonists and amphetamines.

9. A process for preparing a pharmaceutical composition comprising at least one compound according to claim 1, or a tautomeric form thereof, or a physiologically compatible salt thereof, which comprises mixing the compound according to claim 1, or the tautomeric form thereof, or the physiologically tolerated salt thereof, with a pharmaceutically suitable carrier and converting this mixture into a form suitable for administration.

* * * * *